(12) United States Patent
Chang et al.

(10) Patent No.: US 8,404,783 B2
(45) Date of Patent: Mar. 26, 2013

(54) POLYMERS

(75) Inventors: Frank Chang, Suwanee, GA (US);
Norberto Arturo Medina, Suwanee, GA (US)

(73) Assignee: Novartis AG, Basel (CH)

( * ) Notice: Subject to any disclaimer, the term of this patent is extended or adjusted under 35 U.S.C. 154(b) by 712 days.

(21) Appl. No.: 11/825,961

(22) Filed: Jul. 10, 2007

(65) Prior Publication Data
US 2008/0015315 A1    Jan. 17, 2008

Related U.S. Application Data

(60) Provisional application No. 60/830,288, filed on Jul. 12, 2006.

(51) Int. Cl.
*C08F 30/08*    (2006.01)

(52) U.S. Cl. ........................ 525/326.5; 525/100; 525/106; 525/288; 525/342; 525/343; 525/351; 525/326.7; 525/326.9; 525/329.4; 525/329.7; 525/375; 525/389; 526/317.1; 526/279; 526/286; 523/106; 523/107; 524/916

(58) Field of Classification Search .................. 525/100, 525/106, 342, 343, 351, 326.7, 326.9, 329.4, 525/329.7, 375, 386; 526/317.1, 279, 286; 523/106, 103; 524/916
See application file for complete search history.

(56) References Cited

U.S. PATENT DOCUMENTS

| | | | |
|---|---|---|---|
| 3,549,747 A | 12/1970 | Krezanoski et al. | 424/78 |
| 3,639,576 A | 2/1972 | Kaspar et al. | 424/78 |
| 3,882,036 A | 5/1975 | Krezanoski et al. | 252/106 |
| 4,013,576 A | 3/1977 | Loshaek | 252/106 |
| 4,287,175 A | 9/1981 | Katz | 424/78 |
| 4,312,575 A | 1/1982 | Peyman et al. | 351/160 H |
| 4,323,467 A | 4/1982 | Fu | 252/106 |
| 4,444,711 A | 4/1984 | Schad | 264/243 |
| 4,460,534 A | 7/1984 | Boehm et al. | 264/246 |
| 4,500,441 A | 2/1985 | Tanaka et al. | 252/89.1 |
| 4,529,535 A | 7/1985 | Sherman | 252/106 |
| 4,536,554 A | 8/1985 | Lim et al. | 526/264 |
| 4,551,461 A | 11/1985 | Sherman | 514/275 |
| 4,560,491 A | 12/1985 | Sherman | 252/106 |
| 4,568,517 A | 2/1986 | Kaspar et al. | 422/30 |
| 4,626,292 A | 12/1986 | Sherman | 134/26 |
| 4,632,844 A | 12/1986 | Yanagihara et al. | 427/488 |
| 4,746,514 A | 5/1988 | Warne | 424/445 |
| 4,783,488 A | 11/1988 | Ogunbiyi et al. | 514/635 |
| 4,786,436 A | 11/1988 | Ogunbiyi et al. | 252/352 |
| 4,983,702 A | 1/1991 | Mueller et al. | 528/28 |
| 5,008,356 A | 4/1991 | Ishimaru et al. | 526/281 |
| 5,036,971 A | 8/1991 | Seden et al. | 206/5.1 |
| 5,087,392 A | 2/1992 | Burke et al. | 264/2.7 |
| 5,087,677 A | 2/1992 | Brekner et al. | 526/160 |
| 5,141,665 A | 8/1992 | Sherman | 252/106 |
| 5,157,093 A | 10/1992 | Harisiades et al. | 527/301 |
| 5,198,477 A | 3/1993 | von der Haegen et al. | 523/106 |
| 5,260,001 A | 11/1993 | Nandu et al. | 264/2.1 |
| 5,322,667 A | 6/1994 | Sherman | 422/28 |
| 5,364,601 A | 11/1994 | Salpekar | 422/28 |
| 5,382,599 A | 1/1995 | Rupp et al. | 514/547 |
| 5,405,878 A | 4/1995 | Ellis et al. | 422/28 |
| 5,500,144 A | 3/1996 | Potini et al. | 252/174.15 |
| 5,508,317 A | 4/1996 | Muller | 522/85 |
| 5,583,463 A | 12/1996 | Merritt | 327/526 |
| 5,604,189 A | 2/1997 | Zhang et al. | 510/112 |
| 5,656,210 A | 8/1997 | Hill et al. | 264/2.6 |
| 5,665,840 A | 9/1997 | Pohlmann et al. | 526/264 |
| 5,711,823 A | 1/1998 | Ellis et al. | 134/42 |
| 5,712,356 A | 1/1998 | Bothe et al. | 526/264 |
| 5,726,733 A | 3/1998 | Lai et al. | 351/160 |
| 5,731,087 A | 3/1998 | Fan et al. | 428/412 |
| 5,760,100 A | 6/1998 | Nicolson et al. | 523/106 |
| 5,773,396 A | 6/1998 | Zhang et al. | 510/115 |
| 5,789,464 A | 8/1998 | Muller | 523/108 |
| 5,800,412 A | 9/1998 | Zhang et al. | 604/280 |
| 5,807,636 A | 9/1998 | Sheu et al. | 428/403 |
| 5,837,377 A | 11/1998 | Sheu et al. | 428/412 |
| 5,843,346 A | 12/1998 | Morrill | 264/2.5 |
| 5,849,810 A | 12/1998 | Muller | 522/85 |
| 5,849,841 A | 12/1998 | Muhlebach et al. | 525/59 |
| 5,872,086 A | 2/1999 | Ellis et al. | 510/112 |
| 5,882,687 A | 3/1999 | Park et al. | 424/682 |
| 5,894,002 A | 4/1999 | Boneberger et al. | 264/1.36 |

(Continued)

FOREIGN PATENT DOCUMENTS

EP       0315836       6/1989
EP       0 425 436      5/1991

(Continued)

OTHER PUBLICATIONS

Cramer et al., Mechanism and Modeling of a Thiol-Ene Photopolymerization, Macromolecules, 2003, vol. 36, pp. 4631-4636.
Cramer et al., Photopolymerizations of Thiol-Ene Polymers without Photoinitiators, Macromolecules, 2002, vol. 35, pp. 5361-5365.
Cramer et al., Thiol-Ene Photopolymerization Mechanism and Rate Limiting Step Changes for Various Vinyl Functional Group Chemistries, Macromolecules, 2003, vol. 36, pp. 7964-7969.
Evans et al., Free-Radical Ring-Opening Polymerizatino of Cyclic Allylic Sulfides, Macromolecules, 1996, vol. 29, pp. 6983-6989.
Evans et al., Free-Radical Ring-Opening Polymerization of Cyclic Allylic Sulfides. 2. Effect of Substituents on Seven- and Eight-Membered Ring Low Shrink Monomers, Macromolecules, 2000, vol. 33, pp. 6722-6731.

(Continued)

*Primary Examiner* — Robert C Boyle
(74) *Attorney, Agent, or Firm* — Sheng-Hsin Hu; Jian Zhou

(57)    ABSTRACT

The invention relates to novel crosslinkable copolymers which are obtainable by (a) copolymerizing at least two different hydrophilic monomers selected from the group consisting of N,N-dimethyl acrylamide (DMA), 2-hydroxyethyl acrylate (HEA), glycidyl methacrylate (GMA), N-vinylpyrrolidone (NVP), acrylic acid (AA) and a $C_1$-$C_4$-alkoxy polyethylene glycol (meth)acrylate having a weight average molecular weight of from 200 to 1500, and at least one crosslinker comprising two or more ethylenically unsaturated double bonds in the presence of a chain transfer agent having a functional group; and (b) reacting one or more functional groups of the resulting copolymer with an organic compound having an ethylenically unsaturated group.

19 Claims, No Drawings

U.S. PATENT DOCUMENTS

| | | | |
|---|---|---|---|
| 5,936,052 A | 8/1999 | Bothe et al. | 526/264 |
| 5,942,558 A | 8/1999 | Korb | 523/106 |
| 5,998,498 A | 12/1999 | Vanderlaan et al. | 523/107 |
| 6,037,328 A | 3/2000 | Hu et al. | 514/23 |
| 6,039,913 A | 3/2000 | Hirt et al. | 264/331.11 |
| 6,165,408 A | 12/2000 | Steinmann | 264/496 |
| 6,193,369 B1 | 2/2001 | Valint, Jr. et al. | 351/160 H |
| 6,207,628 B1 | 3/2001 | Soyer et al. | 510/112 |
| 6,221,303 B1 | 4/2001 | Steinmann | 264/496 |
| 6,274,133 B1 | 8/2001 | Hu et al. | 424/78.04 |
| 6,303,687 B1 | 10/2001 | Muller | 252/61 |
| 6,348,507 B1 | 2/2002 | Heiler et al. | 514/769 |
| 6,367,929 B1 | 4/2002 | Maiden et al. | 351/160 H |
| 6,428,839 B1 | 8/2002 | Kunzler et al. | 427/2.1 |
| 6,440,366 B1 | 8/2002 | Salpekar et al. | 422/40 |
| 6,451,871 B1 | 9/2002 | Winterton et al. | 523/106 |
| 6,472,489 B1 | 10/2002 | Stockinger | 526/312 |
| 6,479,587 B1 | 11/2002 | Stockinger et al. | 525/131 |
| 6,482,799 B1 | 11/2002 | Tuse et al. | 514/14 |
| 6,492,478 B1 | 12/2002 | Steinmann | 526/258 |
| 6,528,048 B1 | 3/2003 | Koike et al. | 424/78.17 |
| 6,531,432 B2 | 3/2003 | Molock et al. | 510/112 |
| 6,589,665 B2 | 7/2003 | Chabrecek et al. | 428/520 |
| 6,617,291 B1 | 9/2003 | Smith | 510/112 |
| 6,627,124 B1 | 9/2003 | Herbrechtsmeier et al. | 264/1.36 |
| 6,630,243 B2 | 10/2003 | Valint, Jr. et al. | 428/420 |
| 6,634,748 B1 | 10/2003 | Vanderlaan et al. | 351/177 |
| 6,686,330 B2 | 2/2004 | Jordan, IV et al. | 510/475 |
| 6,689,480 B2 | 2/2004 | Shimoyama et al. | 428/451 |
| 6,699,435 B2 | 3/2004 | Salpekar et al. | 422/40 |
| 6,702,983 B2 | 3/2004 | Hu et al. | 422/1 |
| 6,719,929 B2 | 4/2004 | Winterton et al. | 264/1.7 |
| 6,759,491 B2 | 7/2004 | Matyjaszewski et al. | 526/90 |
| 6,793,973 B2 | 9/2004 | Winterton et al. | 427/393.5 |
| 6,805,836 B2 | 10/2004 | Salamone et al. | 422/1 |
| 6,811,805 B2 | 11/2004 | Gilliard et al. | 427/2.1 |
| 6,815,074 B2 | 11/2004 | Aguado et al. | 428/447 |
| 6,822,016 B2 | 11/2004 | McCabe et al. | 523/107 |
| 6,827,966 B2 | 12/2004 | Qiu et al. | 427/2.24 |
| 6,849,671 B2 | 2/2005 | Steffen et al. | 523/107 |
| 6,852,353 B2 | 2/2005 | Qiu et al. | 427/2.24 |
| 6,867,172 B2 | 3/2005 | Alvarez et al. | 510/112 |
| 6,893,685 B2 | 5/2005 | Qiu et al. | 427/407.1 |
| 6,896,926 B2 | 5/2005 | Qiu et al. | 427/2.31 |
| 6,902,812 B2 | 6/2005 | Valint, Jr. et al. | 428/420 |
| 6,926,965 B2 | 8/2005 | Qiu et al. | 428/411.5 |
| 6,943,203 B2 | 9/2005 | Vanderlaan et al. | 523/107 |
| 6,995,192 B2 | 2/2006 | Phelan et al. | 522/90 |
| 7,052,131 B2 | 5/2006 | McCabe et al. | 351/160 |
| 7,091,283 B2 | 8/2006 | Muller et al. | 525/292 |
| 7,165,839 B2 | 1/2007 | Winterton et al. | 351/177 |
| 7,238,750 B2 | 7/2007 | Muller et al. | 525/292 |
| 7,247,692 B2 | 7/2007 | Laredo | 526/279 |
| 7,268,189 B2 | 9/2007 | Muller et al. | 525/292 |
| 7,279,507 B2 | 10/2007 | Hu et al. | 523/108 |
| 7,329,415 B2 | 2/2008 | Lally et al. | 424/429 |
| 7,364,723 B1 | 4/2008 | Nakada et al. | 424/78.04 |
| 2001/0037001 A1* | 11/2001 | Muller et al. | 525/329.4 |
| 2001/0044482 A1 | 11/2001 | Hu et al. | 523/106 |
| 2002/0115578 A1 | 8/2002 | Groemminger | 510/112 |
| 2002/0182315 A1 | 12/2002 | Heiler et al. | 427/162 |
| 2002/0198280 A1* | 12/2002 | Baba et al. | 522/99 |
| 2003/0052424 A1 | 3/2003 | Turner et al. | 264/1.32 |
| 2003/0095230 A1 | 5/2003 | Neely et al. | 351/159 |
| 2003/0096717 A1 | 5/2003 | Xia et al. | 510/112 |
| 2003/0117579 A1 | 6/2003 | Morris et al. | 351/200 |
| 2004/0002556 A1* | 1/2004 | Molock et al. | 522/6 |
| 2004/0028645 A1 | 2/2004 | Chowhan | 424/78.27 |
| 2004/0082052 A1 | 4/2004 | Brown et al. | 435/196 |
| 2004/0115270 A1 | 6/2004 | Jani et al. | 424/486 |
| 2004/0119176 A1 | 6/2004 | Xia et al. | 264/1.32 |
| 2004/0120982 A1 | 6/2004 | Diana et al. | 424/429 |
| 2004/0135967 A1 | 7/2004 | Carney et al. | 351/159 |
| 2004/0186248 A1 | 9/2004 | Vanderlaan et al. | 525/474 |
| 2005/0006255 A1 | 1/2005 | Peck et al. | 206/5.1 |
| 2005/0008676 A1 | 1/2005 | Qiu et al. | 424/429 |
| 2005/0013842 A1 | 1/2005 | Qiu et al. | 424/423 |
| 2005/0047270 A1 | 3/2005 | Wood et al. | 366/170.3 |
| 2005/0058844 A1 | 3/2005 | Rubner et al. | 428/457 |
| 2005/0085591 A1 | 4/2005 | Dozeman et al. | 525/192 |
| 2005/0113549 A1 | 5/2005 | Devlin et al. | 528/44 |
| 2005/0117112 A1 | 6/2005 | Nayiby et al. | 351/160 R |
| 2005/0153056 A1 | 7/2005 | Winterton et al. | 427/2.1 |
| 2005/0154080 A1 | 7/2005 | McCabe et al. | 523/107 |
| 2005/0202549 A1 | 9/2005 | Brown et al. | 435/196 |
| 2005/0237483 A1* | 10/2005 | Phelan | 351/162 |
| 2006/0001184 A1 | 1/2006 | Phelan et al. | 264/1.32 |
| 2006/0055882 A1 | 3/2006 | Phelan | 351/162 |
| 2006/0063852 A1 | 3/2006 | Iwata et al. | 523/106 |
| 2006/0073185 A1 | 4/2006 | Jani et al. | 424/427 |
| 2006/0142169 A1 | 6/2006 | Smith | 510/112 |
| 2007/0010595 A1 | 1/2007 | McCabe et al. | 523/106 |
| 2007/0015205 A1 | 1/2007 | Brown et al. | 435/7.1 |
| 2007/0043140 A1 | 2/2007 | Lorenz et al. | 523/106 |
| 2007/0098768 A1 | 5/2007 | Smith | 424/680 |
| 2008/0015315 A1 | 1/2008 | Chang et al. | 525/326.9 |
| 2008/0021127 A1 | 1/2008 | Muller et al. | 522/99 |
| 2008/0045612 A1 | 2/2008 | Rathore et al. | 516/102 |
| 2008/0167246 A1 | 7/2008 | Smith et al. | 514/13 |
| 2008/0174035 A1 | 7/2008 | Winterton | 264/1.36 |

FOREIGN PATENT DOCUMENTS

| | | |
|---|---|---|
| EP | 0 940 693 | 9/1999 |
| WO | WO 95/00618 | 1/1995 |
| WO | WO 95/34327 | 12/1995 |
| WO | WO 97/20019 | 6/1997 |
| WO | WO 99/33894 | 7/1999 |
| WO | WO 01/34312 | 5/2001 |
| WO | WO 01/71392 | 9/2001 |
| WO | WO 2005/011966 | 2/2005 |

OTHER PUBLICATIONS

Evans et al., New Free-Radical Ring-Opening Acrylate Monomers, Macromolecules, 1994, vol. 27, pp. 7935-7937.

Naciri et al., Molecular Structure and Pretilt Control of Photodimerized-Monolayers (PDML), Journal of Materials Chemistry, 2004, vol. 14, pp. 3468-3473.

Norbornene Technical Data Sheet, 2002, 6 pages.

Okay et al., Molecular Weight Development During Thiol-Ene Photopolymerizations, Macromolcules, 2005, vol. 38, pp. 4501-4511.

Promerus LLC Electronic Materials Technology Tutorial on the Chemistry of Norbornene Monomers and Polymers, Polymerizatio Reactions, and Key Product Application Areas, 19 pages.

Scott et al., Photoinduced Plasticity in Cross-Linked Polymers, Science, 2005, vol. 308, pp. 1615-1617.

PCT International Search Report.

PCT Written Opinion of the International Searching Authority.

* cited by examiner

POLYMERS

This application claims the benefit under 35 USC §119(e) of the filing date of U.S. provisional application No. 60/830,288 filed Jul. 12, 2006.

The present invention relates to novel crosslinkable polymers, to a process for the preparation thereof and to the use thereof for the manufacture of moldings, especially biomedical moldings such as contact lenses.

BACKGROUND OF THE INVENTION

WO 01/71392 discloses polymerizable macromonomers which are obtained by co-polymerizing N,N-dimethyl acrylamide (DMA) and a crosslinker comprising two or more ethylenically unsaturated double bonds in the presence of a chain transfer agent and capping the resultant copolymer with a compound providing a C=C double bond. The macrocomonomers thus obtained may be crosslinked in a suitable mold in order to yield hydrogel moldings, for example contact lenses. According to the above-outlined process valuable polymers with applicability in the field of medical devices may be obtained. However, the synthesis as described above sometimes suffers from some drawbacks affecting the quality of the resulting products. In particular, the first copolymerization step is complex and proceeds in a manner difficult to control. Due to a lack of kinetic control, the reproducibility of the resulting products is sometimes poor. For example, the water contents of the final molding may vary, or the amount of undesired extractables within the molding, for example, reaction products which are present but not incorporated in the polymer matrix of the molding and which therefore may leach out over time, is sometimes high.

In view of this there is a demand to improve the basic concept as outlined in WO 01/71392 and provide new polymers with further improved properties in a more reproducible manner.

SUMMARY OF THE INVENTION

The present invention, in one aspect, provides an actinically crosslinkable prepolymer that is obtained by: (a) copolymerizing a polymerizable mixture to obtain a copolymerization product with first functional groups, wherein the polymerizable mixture comprises a first hydrophilic monomer, at least one polysiloxane-containing crosslinker, a chain transfer agent having a first functional group, a second hydrophilic monomer selected from the group consisting of 2-hydroxyethyl acrylate (HEA), glycidyl methacrylate (GMA), acrylic acid (AA), and a $C_1$-$C_4$-alkoxy polyethylene glycol (meth)acrylate having a weight average molecular weight of from 200 to 1500; and (b) reacting an organic compound with the copolymerization product to form the crosslinkable prepolymer having ethylenically unsaturated groups, wherein the organic compound comprises an ethylenically unsaturated group and a second functional group, wherein the second functional group of the organic compound reacts with one of the first functional groups of the copolymerization product, wherein the second hydrophilic monomer is present in an amount sufficient to produce the resultant prepolymer which, after purification, can be crosslinked actinically or thermally to form a silicone hydrogel material. Preferably, the silicone hydrogel material is characterized by having a reduced amount of non-volatile extractables, preferably about 10% or less, more preferably about 8% or less, even more preferably about 5% or less, of non-volatile extractables.

The invention, in another aspect, provides a process for the manufacture of an actinically crosslinkable or polymerizable prepolymer, which comprises: (a) copolymerizing a polymerizable mixture to obtain a copolymerization product with first functional groups, wherein the polymerizable mixture comprises a first hydrophilic monomer, at least one polysiloxane-containing crosslinker, a chain transfer agent having a first functional group, a second hydrophilic monomer selected from the group consisting of 2-hydroxyethyl acrylate (HEA), glycidyl methacrylate (GMA), acrylic acid (AA), and a $C_1$-$C_4$-alkoxy polyethylene glycol (meth)acrylate having a weight average molecular weight of from 200 to 1500; and (b) reacting an organic compound with the copolymerization product to form the crosslinkable prepolymer having ethylenically unsaturated groups, wherein the organic compound comprises an ethylenically unsaturated group and a second functional group, wherein the second functional group of the organic compound reacts with one of the first functional groups of the copolymerization product, wherein the second hydrophilic monomer is present in an amount sufficient to produce the resultant prepolymer which, after purification, can be crosslined actinically or thermally to form a silicone hydrogel material. Preferably, the silicone hydrogel material is characterized by having a reduced amount of non-volatile extractables, preferably about 10% or less, more preferably about 8% or less, even more preferably about 5% or less, of non-volatile extractables.

The invention, in still another aspect, provides a process for manufacturing an actinically crosslinkable prepolymer, which comprises: (1) obtaining a reaction mixture comprising a first hydrophilic monomer, at least one polysiloxane-containing crosslinker, a second hydrophilic monomer selected from the group consisting of 2-hydroxyethyl acrylate (HEA), glycidyl methacrylate (GMA), acrylic acid (AA), and a $C_1$-$C_4$-alkoxy polyethylene glycol (meth)acrylate having a weight average molecular weight of from 200 to 1500, and a chain transfer agent having a first functional group and present in an amount to have a desired initial concentration; (2) adjusting the temperature of the reaction mixture in order to start the polymerization reaction; (3) dosing the chain transfer agent to the reaction mixture at a rate sufficient to keep the initial concentration approximately constant until a desired total amount of the chain transfer agent is added; (4) following the completion of the chain transfer agent dosing maintaining the reaction mixture at the reaction temperature in order to complete the reaction so as to obtain a copolymerization product with first functional groups; and (5) reacting an organic compound with the copolymerization product to form the crosslinkable prepolymer having ethylenically unsaturated groups, wherein the organic compound comprises an ethylenically unsaturated group and a second functional group, wherein the second functional group of the organic compound reacts with one of the first functional groups of the copolymerization product, wherein said crosslinkable prepolymer can be crosslinked to form a silicone hydrogel material.

The invention, in still another aspect, provides a biomedical molding, in particular an ophthalmic molding such as a contact lens, intraocular lens, or artificial cornea, which is obtained by crosslinking an above-mentioned actinically crosslinkable prepolymer.

These and other aspects of the invention will become apparent from the following description of the presently preferred embodiments.

DETAILED DESCRIPTION OF THE PREFERRED EMBODIMENTS

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well known and commonly employed in the art.

"Contact Lens" refers to a structure that can be placed on or within a wearer's eye. A contact lens can correct, improve, or alter a user's eyesight, but that need not be the case. A contact lens can be of any appropriate material known in the art or later developed, and can be a soft lens, a hard lens, or a hybrid lens. A "silicone hydrogel contact lens" refers to a contact lens comprising a silicone hydrogel material.

A "hydrogel" or "hydrogel material" refers to a polymeric material which can absorb at least 10 percent by weight of water when it is fully hydrated.

A "silicone hydrogel" or "silicone hydrogel material" refers to a silicone-containing polymeric material which can absorb at least 10 percent by weight of water when it is fully hydrated.

"Hydrophilic," as used herein, describes a material or portion thereof that will more readily associate with water than with lipids.

A "monomer" means a low molecular weight compound that can be polymerized via free radical reaction. Low molecular weight typically means average molecular weights less than 700 Daltons. A monomer has an ethylenically unsaturated group and can be polymerized actinically or thermally.

A "macromer" refers to a medium and high molecular weight compound which can be polymerized and/or crosslinked via free radical reaction. Medium and high molecular weight typically means average molecular weights greater than 700 Daltons. A macromer has one or more ethylenically unsaturated groups and can be polymerized actinically or thermally.

A "polysiloxane" refers to a moiety of $$\left[\begin{array}{c} R_1 \\ | \\ Si-O \\ | \\ R_2 \end{array}\right]_n$$

in which $R_1$ and $R_2$ are independently a monovalent $C_1$-$C_{10}$ alkyl, $C_1$-$C_{10}$ ether, $C_1$-$C_{10}$ fluoroalkyl, $C_1$-$C_{10}$ fluoroether, or $C_6$-$C_{18}$ aryl radical, which may comprise hydroxy group, primary, secondary, or tertiary amine group, carboxy group, or carboxylic acid; n is an integer of 4 or higher.

A "polysiloxane-containing crosslinker" refers to a compound that comprises a polysiloxane moiety and at least two ethylenically unsaturated groups.

The term "olefinically unsaturated group" or "ethylenticaly unsaturated group" is employed herein in a broad sense and is intended to encompass any groups containing a >C=C< group. Exemplary ethylenically unsaturated groups include without limitation acryloyl, methacryloyl, allyl, vinyl, styrenyl, or other C=C containing groups.

As used herein, "actinically" in reference to curing, crosslinking or polymerizing of a polymerizable composition, a prepolymer or a material means that the curing (e.g., crosslinked and/or polymerized) is performed by actinic irradiation, such as, for example, UV irradiation, ionized radiation (e.g. gamma ray or X-ray irradiation), microwave irradiation, and the like. Thermal curing or actinic curing methods are well-known to a person skilled in the art.

The term "fluid" as used herein indicates that a material is capable of flowing like a liquid.

A "hydrophilic monomer" refers to a monomer which can be polymerized to form a polymer that can absorb at least 10 percent by weight of water when fully hydrated.

A "hydrophobic monomer", as used herein, refers to a monomer which can be polymerized to form a polymer that can absorb less than 10 percent by weight water when fully hydrated.

A "prepolymer" refers to a starting polymer which contains three or more ethylenically unsaturated groups and can be cured (e.g., crosslinked) actinically to obtain a crosslinked polymer having a molecular weight much higher than the starting polymer.

A "silicone-containing prepolymer" refers to a prepolymer which contains silicone and ethylenically unsaturated groups.

"Molecular weight" of a polymeric material (including monomeric or macromeric materials), as used herein, refers to the number-average molecular weight unless otherwise specifically noted or unless testing conditions indicate otherwise.

"Polymer" means a material formed by polymerizing one or more monomers.

As used herein, the term "ethylenically functionalize" in reference to a copolymer is intended to describe that one or more ethylenically unsaturated groups have been covalently attached to a copolymer through the pendant or terminal functional groups of the copolymer according to a coupling process.

As used herein, the term "multiple" refers to three or more.

A "photoinitiator" refers to a chemical that initiates radical crosslinking/polymerizing reaction by the use of light. Suitable photoinitiators include, without limitation, benzoin methyl ether, diethoxyacetophenone, a benzoylphosphine oxide, 1-hydroxycyclohexyl phenyl ketone, Darocure® types, and Irgacure® types, preferably Darocure® 1173, and Irgacure® 2959.

A "thermal initiator" refers to a chemical that initiates radical crosslinking/polymerizing reaction by the use of heat energy. Examples of suitable thermal initiators include, but are not limited to, 2,2'-azobis(2,4-dimethylpentanenitrile), 2,2'-azobis(2-methylpropanenitrile), 2,2'-azobis(2-methylbutanenitrile), peroxides such as benzoyl peroxide, and the like. Preferably, the thermal initiator is 2,2'-azobis(isobutyronitrile) (AIBN).

A "spatial limitation of actinic radiation" refers to an act or process in which energy radiation in the form of rays is directed by, for example, a mask or screen or combinations thereof, to impinge, in a spatially restricted manner, onto an area having a well defined peripheral boundary. For example, a spatial limitation of UV radiation can be achieved by using a mask or screen that has a transparent or open region (unmasked region) surrounded by a UV impermeable region (masked region), as schematically illustrated in FIGS. 1-9 of U.S. Pat. No. 6,627,124 (herein incorporated by reference in its entirety). The unmasked region has a well defined peripheral boundary with the unmasked region. The energy used for the crosslinking is radiation energy, especially UV radiation, gamma radiation, electron radiation or thermal radiation, the radiation energy preferably being in the form of a substantially parallel beam in order on the one hand to achieve good restriction and on the other hand efficient use of the energy.

"Visibility tinting" in reference to a lens means dying (or coloring) of a lens to enable the user to easily locate a lens in a clear solution within a lens storage, disinfecting or cleaning container. It is well known in the art that a dye and/or a pigment can be used in visibility tinting a lens.

"Surface modification" or "surface treatment", as used herein, means that an article has been treated in a surface treatment process (or a surface modification process) prior to or posterior to the formation of the article, in which (1) a coating is applied to the surface of the article, (2) chemical species are adsorbed onto the surface of the article, (3) the chemical nature (e.g., electrostatic charge) of chemical groups on the surface of the article are altered, or (4) the surface properties of the article are otherwise modified. Exemplary surface treatment processes include, but are not limited to, a surface treatment by energy (e.g., a plasma, a static electrical charge, irradiation, or other energy source), chemical treatments, the grafting of hydrophilic monomers or macromers onto the surface of an article, mold-transfer coating process disclosed in U.S. Pat. No. 6,719,929 (herein incorporated by reference in its entirety), the incorporation of wetting agents into a lens formulation for making contact lenses proposed in U.S. Pat. Nos. 6,367,929 and 6,822,016 (herein incorporated by references in their entireties), reinforced mold-transfer coating disclosed in U.S. Patent Application No. 60/811,949 (herein incorporated by reference in its entirety), and LbL coating. A preferred class of surface treatment processes are plasma processes, in which an ionized gas is applied to the surface of an article. Plasma gases and processing conditions are described more fully in U.S. Pat. Nos. 4,312,575 and 4,632,844, which are incorporated herein by reference. The plasma gas is preferably a mixture of lower alkanes and nitrogen, oxygen or an inert gas.

"LbL coating", as used herein, refers to a coating that is not covalently attached to a contact lens or a mold half and is obtained through a layer-by-layer ("LbL") deposition of polyionic (or charged) and/or non-charged materials on the lens or mold half. An LbL coating can be composed of one or more layers.

As used herein, a "polyionic material" refers to a polymeric material that has a plurality of charged groups or ionizable groups, such as polyelectrolytes, p- and n-type doped conducting polymers. Polyionic materials include both polycationic (having positive charges) and polyanionic (having negative charges) materials.

Formation of an LbL coating on a contact lens or mold half may be accomplished in a number of ways, for example, as described in U.S. Pat. Nos. 6,451,871, 6,719,929, 6,793,973, 6,811,805, 6,896,926 (herein incorporated by references in their entirety).

An "antimicrobial agent", as used herein, refers to a chemical that is capable of decreasing or eliminating or inhibiting the growth of microorganisms such as that term is known in the art.

"Antimicrobial metals" are metals whose ions have an antimicrobial effect and which are biocompatible. Preferred antimicrobial metals include Ag, Au, Pt, Pd, Ir, Sn, Cu, Sb, Bi and Zn, with Ag being most preferred.

"Antimicrobial metal-containing nanoparticles" refer to particles having a size of less than 1 micrometer and containing at least one antimicrobial metal present in one or more of its oxidation states.

"Antimicrobial metal nanoparticles" refer to particles which is made essentially of an antimicrobial metal and have a size of less than 1 micrometer. The antimicrobial metal in the antimicrobial metal nanoparticles can be present in one or more of its oxidation states. For example, silver-containing nanoparticles can contain silver in one or more of its oxidation states, such as $Ag^0$, $Ag^{1+}$, and $Ag^{2+}$.

The "oxygen transmissibility" of a lens, as used herein, is the rate at which oxygen will pass through a specific ophthalmic lens. Oxygen transmissibility, Dk/t, is conventionally expressed in units of barrers/mm, where t is the average thickness of the material [in units of mm] over the area being measured and "barrer/mm" is defined as:

$$[(cm^3 oxygen)/(cm^2)(sec)(mmHg)] \times 10^{-9}$$

The intrinsic "oxygen permeability", Dk, of a lens material does not depend on lens thickness. Intrinsic oxygen permeability is the rate at which oxygen will pass through a material. Oxygen permeability is conventionally expressed in units of barrers, where "barrer" is defined as:

$$[(cm^3 oxygen)(mm)/(cm^2)(sec)(mmHg)] \times 10^{-10}$$

These are the units commonly used in the art. Thus, in order to be consistent with the use in the art, the unit "barrer" will have the meanings as defined above. For example, a lens having a Dk of 90 barrers ("oxygen permeability barrers") and a thickness of 90 microns (0.090 mm) would have a Dk/t of 100 barrers/mm (oxygen transmissibility barrers/mm). In accordance with the invention, a high oxygen permeability in reference to a material or a contact lens characterized by apparent oxygen permeability of at least 40 barrers or larger measured with a sample (film or lens) of 100 microns in thickness according to a coulometric method described in Examples.

The "ion permeability" through a lens correlates with both the Ionoflux Diffusion Coefficient and the Ionoton Ion Permeability Coefficient.

The Ionoflux Diffusion Coefficient, D, is determined by applying Fick's law as follows:

$$D = -n'/(A \times dc/dx)$$

where
$n'$=rate of ion transport [mol/min]
$A$=area of lens exposed [mm$^2$]
$D$=Ionoflux Diffusion Coefficient [mm$^2$/min]
$dc$=concentration difference [mol/L]
$dx$=thickness of lens [mm]

The Ionoton Ion Permeability Coefficient, P, is then determined in accordance with the following equation:

$$\ln(1 - 2C(t)/C(0)) = -2APt/Vd$$

where:
$C(t)$=concentration of sodium ions at time t in the receiving cell
$C(0)$=initial concentration of sodium ions in donor cell
$A$=membrane area, i.e., lens area exposed to cells
$V$=volume of cell compartment (3.0 ml)
$d$=average lens thickness in the area exposed
$P$=permeability coefficient An Ionoflux Diffusion Coefficient, D, of greater than about $1.5 \times 10^{-6}$ mm$^2$/min is preferred, while greater than about $2.6 \times 10^{-6}$ mm$^2$/min is more preferred and greater than about $6.4 \times 10^{-6}$ mm$^2$/min is most preferred.

It is known that on-eye movement of the lens is required to ensure good tear exchange, and ultimately, to ensure good corneal health. Ion permeability is one of the predictors of on-eye movement, because the permeability of ions is believed to be directly proportional to the permeability of water.

"Non-volatile extractables" refers materials that can be extracted from a hydrogel material with isopropanol or methanol, preferably with methanol. The amount of non-volatile extractables in a hydrogel material is determined according to the procedure described in Example 3.

A "reduced amount of non-volatile extractables" in reference to a silicone hydrogel material means that the amount of non-volatile extractables in a hydrogel material obtained from crosslinking of a prepolymer is smaller than that of a control hydrogel material obtained from crosslinking of a control hydrogel material. In accordance with the invention, the testing prepolymer differs from the control prepolymer mainly in that a first polymerizable composition for making the testing prepolymer contains, in addition to a first hydrophilic monomer (alkylacrylamide), a second hydrophilic monomer as reaction control agent whereas a second polymerizable composition for making the control prepolymer is substantially similar to the first composition but without the second hydrophilic monomer.

In general, the invention is directed to a class of actinically crosslinkable silicone-containing prepolymers, which can be used to prepare silicone hydrogel contact lenses, in particularly according to the Lightstream Technology™ (CIBA Vision). This class of prepolymers are prepared by a two-stage process: (1) copolymerizing, via free radical polymerization mechanism, a composition in the presence of a chain transfer agent with a functional group to obtain a copolymer with the functional groups; and (2) covalently attaching ethylenically unsaturated groups to the functional groups of the copolymer obtained in stage 1. Surprisingly, it has now been found that the polymerization reaction of a hydrophilic monomer such as alkylacrylamide in the presence of a polysiloxane-containing crosslinker and a chain transfer agent is running much smoother and better controllable if a second hydrophilic monomer is present as a moderator to control polymerization reaction, as shown by the facts that there is less amount of non-volatile extractables in contact lenses made by crosslinking the resultant prepolymer.

Although the inventors do not wish to be bound by any particular theory, it is believed that the extent of the incorporation of the chain transfer agent in the copolymer at stage 1 of the process for making a prepolymer may has significant effects on the non-volatile extractables in a hydrogel lens obtained by crosslinked the prepolymer. This is partly due the fact the ethylenically unsaturated groups must be introduced to the copolymer through its functional groups which in turn is derived from the incorporation of the chain transfer agent with the functional group. It is also believed that the extent of the incorporation of the chain transfer agent may depend upon ratio of free radical propagation reaction to free radical chain reaction in the polymerization of the composition. A chain transfer agent (containing a —SH group) primarily involves only in free radical propagation. Where the free radical chain reaction is too fast (i.e., among monomers and polysiloxane-containing crosslinker), it becomes so predominant over the free radical propagation that only insufficient amount of chain transfer agent may be incorporated in the copolymer. By having a second hydrophilic monomer which has a free radical chain reaction slower than that of alkylacrylamide, one may increase the extent of free radical propagation so as to increase the extent of incorporation of the chain transfer agent.

The present invention, in one aspect, provides an actinically crosslinkable prepolymer that is obtained by: (a) copolymerizing a polymerizable mixture to obtain a copolymerization product with first functional groups, wherein the polymerizable mixture comprises a first hydrophilic monomer, at least one polysiloxane-containing crosslinker, a chain transfer agent having a first functional group, a second hydrophilic monomer selected from the group consisting of 2-hydroxyethyl acrylate (HEA), glycidyl methacrylate (GMA), N-vinylpyrrolidone (NVP), acrylic acid (AA), and a $C_1$-$C_4$-alkoxy polyethylene glycol (meth)acrylate having a weight average molecular weight of from 200 to 1500; and (b) reacting an organic compound with the copolymerization product to form the crosslinkable prepolymer having ethylenically unsaturated groups, wherein the organic compound comprises an ethylenically unsaturated group and a second functional group, wherein the second functional group of the organic compound reacts with one of the first functional groups of the copolymerization product, wherein the second hydrophilic monomer is present in an amount sufficient to produce the resultant prepolymer which, after purification, can be crosslined actinically or thermally to form a silicone hydrogel material. Preferably, the silicone hydrogel material is characterized by having a reduced amount of non-volatile extractables, preferably about 10% or less, more preferably about 8% or less, even more preferably about 5% or less, of non-volatile extractables.

Preferably, the first hydrophilic monomer is an alkylacrylamide. In accordance with the invention, an alkylacrylamide refers to a ($C_1$-$C_4$-alkyl)acrylamide or a N,N-di-($C_1$-$C_4$-alkyl)acrylamide, preferably N,N-dimethylacrylamide or isopropylacrylamide.

A suitable $C_1$-$C_4$-alkoxy polyethylene glycol (meth)acrylate hydrophilic monomer is, for example, a $C_1$-$C_4$-alkoxy polyethylene glycol acrylate or a $C_1$-$C_4$-alkoxy polyethylene glycol methacrylate each having a weight average molecular weight of from 200 to 1500, preferably from 300 to 1000, more preferably from 300 to 750 and in particular from 350 to 650. An especially preferred polyethylene glycol hydrophilic monomer is a $C_1$-$C_2$-alkoxy polyethylene glycol acrylate and in particular a methoxy polyethylene glycol acrylate having a molecular weight within the above given ranges.

The second hydrophilic monomers is preferably selected from the group consisting of HEA, GMA, NVP, AA and a $C_1$-$C_4$-alkoxy polyethylene glycol (meth)acrylate having a weight average molecular weight of from 200 to 1500, more preferably from the group consisting of HEA, GMA, AA and a $C_1$-$C_2$-alkoxy polyethylene glycol acrylate having a weight average molecular weight of from 200 to 1500, even more preferably from the group consisting of HEA, AA and a methoxy polyethylene glycol acrylate having a weight average molecular weight of from 300 to 1000. According to one preferred embodiment of the invention a mixture of DMA and HEA is used as hydrophilic monomers. According to a further preferred embodiment of the invention a mixture of DMA, HEA and AA is used as hydrophilic monomers. According to still another preferred embodiment of the invention a mixture of DMA and GMA is used as hydrophilic monomers. Still a further preferred embodiment is directed to a mixture of DMA and a $C_1$-$C_4$-alkoxy polyethylene glycol (meth)acrylate, wherein the above given meanings and preferences apply, as hydrophilic monomers.

In general, DMA is present as the first hydrophilic monomers in an amount of from 40 to 90%, preferably from 50 to 85%, more preferably from 55 to 80%, even more preferably from 70 to 80% and in particular from 70 to 75%, each by weight relative to the total weight of hydrophilic monomers.

HEA, NVP, GMA and the $C_1$-$C_4$-alkoxy polyethylene glycol (meth)acrylate, if present as the second hydrophilic monomer, are each independently present in an amount of, for example, from 10 to 60%, preferably from 15 to 50%, more preferably from 20 to 45%, even more preferably from 20 to 30% and in particular from 25 to 30%, each by weight relative to the total weight of hydrophilic monomers.

AA, if present as the second hydrophilic monomer, is present in an amount of, for example, from 0.5 to 10%, preferably from 1 to 5%, and in particular from 1 to 3%, each by weight relative to the total weight of hydrophilic monomers.

One preferred embodiment concerns a mixture of hydrophilic monomers consisting of 50 to 80% DMA and 20 to 50% HEA each by weight relative to the total weight of hydrophilic monomers. A further preferred embodiment concerns a mixture of hydrophilic monomers consisting of 50 to 80% DMA, 20 to 45% HEA and 1 to 5% M, each by weight relative to the total weight of hydrophilic monomers. Still a further preferred embodiment concerns a mixture of hydrophilic monomers consisting of 50 to 80% DMA and 20 to 50% GMA, each by weight relative to the total weight of hydrophilic monomers. Still a further preferred embodiment concerns a mixture of hydrophilic monomers consisting of 50 to 80% DMA and 20 to 50% $C_1$-$C_4$-alkoxy polyethylene glycol (meth)acrylate, wherein the above-given meaning and preferences apply, each by weight relative to the total weight of hydrophilic monomers.

The choice of crosslinker employed in step (a) may vary within wide limits and is strongly dependent upon the intended use.

One group of suitable crosslinkers comprises polysiloxanes. A suitable polysiloxane crosslinker may comprise two or more, preferably from 2 to 8, more preferably from 2 to 4, even more preferably two, ethylenically unsaturated moieties bound terminally or pendently to silicon atoms by means of a suitable bridge member. The weight-average molecular weight of the polysiloxane crosslinker is, for example, from 500 to 50000, preferably from 1000 to 25000, more preferably from 2500 to 15000 and in particular from 2500 to 12000.

A preferred polysiloxane crosslinker is, for example, of formula

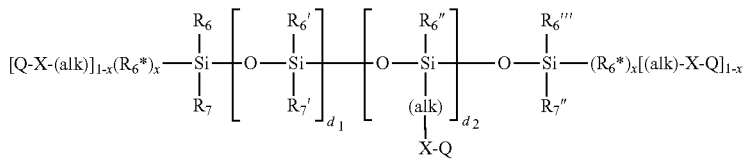

(1)

in which (alk) is alkylene having up to 20 carbon atoms which may be interrupted by —O—; X is —O— or —$NR_8$—, $R_8$ is hydrogen or $C_1$-$C_6$-alkyl, Q is an organic radical comprising a crosslinkable or polymerizable group, 80-100% of the radicals $R_6$, $R_6'$, $R_6''$, $R_6'''$, $R_6^*$, $R_7$, $R_7'$ and $R_7''$, independently of one another, are $C_1$-$C_8$-alkyl and 0-20% of the radicals $R_6$, $R_6'$, $R_6''$, $R_6'''$, $R_6^*$, $R_7$, $R_7'$ and $R_7''$, independently of one another, are unsubstituted or $C_1$-$C_4$ alkyl- or $C_1$-$C_4$—alkoxy-substituted phenyl, fluoro($C_1$-$C_{18}$-alkyl), cyano($C_1$-$C_{12}$-alkyl), hydroxy-$C_1$-$C_6$-alkyl or amino-$C_1$-$C_6$-alkyl, x is the number 0 or 1, $d_1$ is an integer of from 5 to 700, $d_2$ is an integer from 0 to 8 if x is 0, and is 2 to 10 if x is 1, and the sum of ($d_1$+$d_2$) is from 5 to 700.

In a preferred meaning, the sum of ($d_1$+$d_2$) is an integer from 10 to 500, more preferably 10 to 300, particularly preferably 20 to 200 and in particular 20 to 100. Preferably, $d_2$ and x are each 0. According to another preferred embodiment, x is 0 and $d_2$ is an integer from 1 to 4. According to still another preferred embodiment, x is 1 and $d_2$ is an integer from 2 to 4.

Preferably 90 to 100% of the radicals $R_6$, $R_6'$, $R_6''$, $R_6'''$, $R_6^*$, $R_7$, $R_7'$ and $R_7''$ are $C_1$-$C_4$-alkyl, in particular methyl, and 0 to 10% of the radicals $R_6$, $R_6'$, $R_6''$, $R_6'''$, $R_6^*$, $R_7$, $R_7'$ and $R_7''$ are each independently amino-$C_1$-$C_4$-alkyl or hydroxy-$C_1$-$C_4$-alkyl.

A preferred embodiment of suitable polysiloxane crosslinkers encompasses a radical of the above formula (1), wherein x is 0, $d_2$ is 0, $d_1$ is an integer from 5 to 700, preferably 10 to 500, more preferably 10 to 300, even more preferably 20 to 200 and in particular preferably 20 to 100, $R_6$, $R_6'$, $R_6''$, $R_7$, $R_7'$ and $R_7''$ are each independently of the another $C_1$-$C_4$-alkyl, in particular methyl, and for (alk), X and Q the above and below given meanings and preferences apply.

(alk) is preferably $C_2$-$C_8$-alkylene, which may be interrupted by —O— and more preferably $C_2$-$C_6$-alkylene which may be interrupted by —O—. Examples of particular preferred radicals (alk) are linear or branched $C_2$-$C_6$ alkylene or a radical —($CH_2$)$_{1-3}$—O—($CH_2$)$_{1-3}$—, especially $C_2$-$C_4$-alkylene such as 1,2-ethylene, 1,3-propylene or 1,4-butylene, or a radical —($CH_2$)$_{2-3}$—O—($CH_2$)$_{2-3}$—, in particular —($CH_2$)$_2$—O—($CH_2$)$_2$— or —($CH_2$)$_2$—O—($CH_2$)$_3$—.

$R_8$ is preferably hydrogen or $C_1$-$C_4$-alkyl, and particularly hydrogen or $C_1$-$C_2$-alkyl. X is preferably —O—, —NH— or —N($C_1$-$C_2$-alkyl)-, in particular —O— or especially —NH—.

Q is, for example, a radical of formula

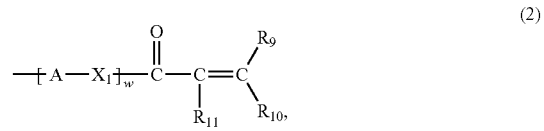

(2)

wherein $R_{11}$ is hydrogen or $C_1$-$C_4$-alkyl, $R_9$ and $R_{10}$ are each independently of the other hydrogen, $C_1$-$C_4$-alkyl, phenyl, carboxy or halogen, $X_1$ is —O— or —NH—, w is the number 0 or 1, and A is a bivalent radical

(3a)

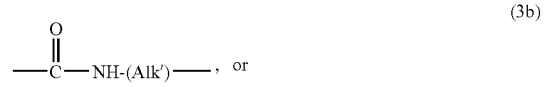

(3b)

(3c)

wherein (Alk) is linear or branched $C_3$-$C_6$-alkylene, (Alk') is linear or branched $C_2$-$C_{12}$-alkylene, and (Alk") is linear or branched $C_1$-$C_6$-alkylene.

$R_{11}$ is preferably hydrogen or methyl. Each of $R_9$ and $R_{10}$ independently of the other is preferably hydrogen, carboxy, chlorine, methyl or phenyl. In a preferred embodiment of the invention, $R_9$ is hydrogen or methyl and $R_{10}$ is hydrogen or carboxy. Most preferably, $R_9$ and $R_{10}$ are each hydrogen. The radical —[(Alk)—OH]— in formula (3a) is preferably 2-hydroxy-1,3-propylene. (Alk') is preferably $C_2$-$C_6$-alkylene, more preferably $C_2$-$C_4$-alkylene and in particular ethylene. (Alk") is preferably $C_1$-$C_3$-alkylene, for example methylene or in particular 1,1-dimethylmethylene.

Especially preferred radicals -Q correspond to formula

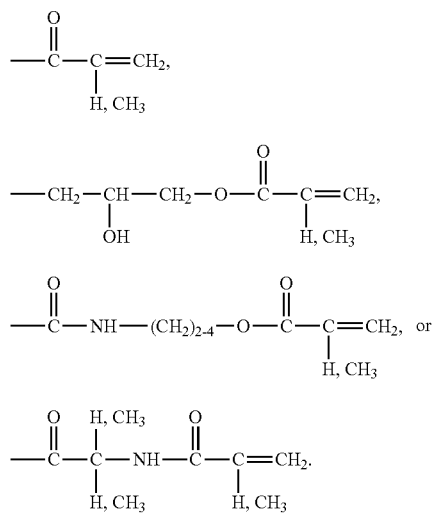

A preferred polysiloxane crosslinker corresponds to formula

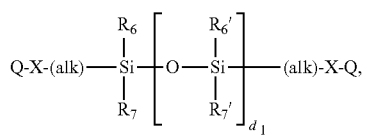

wherein $R_6$, $R_6'$, $R_7$ and $R_7'$ are each $C_1$-$C_4$-alkyl, in particular methyl, $d_1$ is an integer from 10 to 500, preferably 10 to 300, more preferably 20 to 200 and in particular 25 to 150, (alk) is linear or branched $C_2$-$C_6$ alkylene or a radical —$(CH_2)_{1-3}$—O—$(CH_2)_{1-3}$—, X is —O— or in particular —NH— and Q is a radical of the above formula (2a), (3a'), (3b') or (3c'), in particular (2a) or (3b').

The polysiloxane crosslinkers are known or may be obtained according to methods known per se. For example, the compounds of formula (1) or (1a) may be prepared by reacting the corresponding compounds of formula (1) or (1a), wherein Q is hydrogen with a compound of formula (4a)-(4e) as mentioned below under conditions as described below for the preparation of the polymerizable prepolymers. The compounds of formula (1) or (1a), wherein Q is hydrogen, are commercially available, for example, from Wacker or Shin-Etsu.

Instead of employing just one crosslinker in the manufacture of the prepolymers of the invention, two or more different crosslinkers may be used. For example, a mixture of two or more of the above-mentioned polysiloxane crosslinkers having different molecular weights may be advantageous. One preferred embodiment concerns the use of a mixture of two different polysiloxane crosslinkers, one having a weight-average molecular weight of from 1000 to 5000, in particular from 2500 to 5000, and the second one having a weight-average molecular weight of from 8000 to 25000, in particular from 10000 to 15000. In case of a mixture of two polysiloxane crosslinkers of different molecular weight, the weight ratio of low molecular weight to high molecular weight crosslinker is, for example, from 10:90 to 50:50, and is preferably from 20:80 to 40:60.

The chain transfer agent used in step (a) controls the molecular weight of the resulting prepolymer and provides functionality for subsequent addition of a polymerizable or crosslinkable group. The chain transfer agent may comprise one or more thiol groups, for example two or most preferably one thiol group. Suitable chain transfer agents include organic primary thiols or mercaptans having a further functional group such as, for example, hydroxy, amino, N—$C_1$-$C_6$-alkylamino, carboxy or a suitable derivative thereof. A preferred chain transfer agent is a cycloaliphatic or preferably aliphatic thiol having from 2 to about 24 carbon atoms and having a further functional group selected from amino, hydroxy and carboxy; accordingly, the preferred chain transfer agents are aliphatic mercapto carboxylic acids, hydroxymercaptans or aminomercaptans. Examples of particularly preferred chain transfer agents are thioglycolic acid, 2-mercaptoethanol and especially 2-aminoethane thiol (cysteamine). In case of an amine or a carboxylic acid, the chain transfer agent may be in form of the free amine or acid or, preferably, in form of a suitable salt thereof, for example a hydrochloride in case of an amine or a sodium, potassium or amine salt in case of an acid. An example for a chain transfer agent having more than one thiol group is the reaction product of one equivalent of diethylene triamine with about two equivalents of γ-thiobutyrolactone.

The weight ratio of the hydrophilic monomers and crosslinker(s) in step (a) may be chosen within wide limits and is strongly dependant on the intended use. For example, a weight ratio of from 35 to 70% crosslinker(s): 65 to 30% hydrophilic monomers has proven as practicable for biomedical purposes. A preferred range is from 35 to 65% crosslinker(s): 65 to 35% by weight of hydrophilic monomers. A particularly preferred weight range is from 40 to 65% crosslinker(s): 60 to 35% hydrophilic monomers. The chain transfer agent may be present in the reaction mixture in an amount of, for example, from 0.5 to 5%, preferably from 1 to 4%, and in particular from 1.5 to 3.5% by weight, relative to the combined weight of crosslinkers and hydrophilic monomers.

The copolymerization step (a) may be carried out in the presence of a solvent. The solvent choice is dependent on the monomers and crosslinkers used. Preferred solvents include $C_1$-$C_4$-alcohols such as methanol, ethanol or n- or isopropanol; cyclic ether such as tetrahydrofurane or dioxane; ketones such as methyl ethyl ketone; optionally halogenated hydrocarbons such as toluene, chloroform or dichloromethane; and mixtures of these solvents. Preferred solvents are ethanol, THF, n- or isopropanol or a mixture of ethanol and THF. The contents of polymerizable components within the solution may vary within wide limits. Advantageously the total of polymerizable components within the solution is in the range of ≦30% by weight, preferably ≦25% by weight and most preferably from 10 to 20% by weight, based in each case on the total weight of the solution.

The copolymerization of the hydrophilic monomer(s) and crosslinker in step (a) may be induced photochemically or preferably thermally. Suitable thermal polymerization initiators are known to the skilled artisan and comprise, for example peroxides, hydroperoxides, azo-bis(alkyl- or cycloalkylnitriles), persulfates, percarbonates or mixtures thereof. Examples are benzoylperoxide, tert.-butyl peroxide, di-tert.-butyl-diperoxyphthalate, tert.-butyl hydroperoxide, azo-bis(isobutyronitrile) (AIBN), 1,1-azodiisobutyramidine, 1,1'-azo-bis(1-cyclohexane-carbonitrile), 2,2'-azo-bis(2,4-dimethylvaleronitrile) and the like. The polymerization is carried out conveniently in an above-mentioned solvent at elevated temperature, for example at a temperature of from 25 to 100° C. and preferably 40 to 80° C. The reaction time may vary within wide limits, but is conveniently, for example, from 1 to 24 hours or preferably from 2 to 12 hours. It is advantageous to previously degas the components and solvents used in the polymerization reaction and to carry out said copolymerization reaction under an inert atmosphere, for example under a nitrogen or argon atmosphere.

The copolymerization reaction may be carried out batch wise, that is to say, the hydrophilic monomers, crosslinker(s), solvents, polymerization initiator and chain transfer agent are all added in their entirety to one reaction vessel and the reaction takes places, for example, at room temperature, or preferably at an elevated temperature, for example at a temperature from 35 to 80° C. and preferably from 50 to 80° C., for a period of time which may vary within wide limits dependent on the specific reactivity of the reactants. In general, a reaction time from 8 to 20 hours is enough to complete the reaction.

In a preferred embodiment of the invention, all the reactants except the chain transfer agent are added to the reaction vessel each in their entirety, and the chain transfer agent is then metered in at a rate which is dependent on the reaction progress. For example, the reaction progress may be monitored using gas chromatography, which in turn triggers the addition of chain transfer agent. For example, it is preferred to add a first portion of the chain transfer agent, for example from 10 to 40% and preferably from 15 to 35% by weight of the total weight of chain transfer agent, to the reaction mixture comprising the polymerizable material and the polymerization catalyst, then start the reaction, for example, by adjusting the temperature of the reaction mixture, in particular by heating up the reaction mixture to an elevated temperature as mentioned above, and then dosing the remaining chain transfer agent to the reaction mixture at a rate sufficient to keep the initial chain transfer agent concentration in the reaction vessel comparable to the desired initial concentration until a desired total amount of the chain transfer agent is added. Following the completion of the chain transfer agent dosing, the reaction mixture is advantageously maintained at the reaction temperature for some additional time in order to complete the reaction. The time period for dosing is dependent on the reactivity of the monomers. In general, the dosing reaction is carried out at an elevated temperature, for example at a temperature of from 35 to 80° C. and preferably between 50 and 80° C.

Surprisingly, the polymerization reaction of the two or more hydrophilic monomers in the presence of a crosslinker proceeds in a very controlled and reproducible manner and yields optical clear well-defined copolymers which may be worked up in conventional manner using for example extraction, precipitation, ultrafiltration and the like techniques.

The weight average molecular weight of the resulting copolymers is strongly dependent, for example, on the amount of chain transfer agent used. A weight average molecular weight of, for example, from 500 to 200000, preferably from 750 to 100000, more preferably from 750 to 50000, and in particular from 1000 to 25000 has proven as valuable.

The organic compound having an ethylenically unsaturated double bond according to step (b) is, for example, an ethylenically unsaturated compound having from 2 to 18 C-atoms which is substituted by a reactive group that is co-reactive to the functional group of the chain transfer agent. Examples of such co-reactive groups are a carboxy, carboxylic acid ester, carboxylic acid anhydride, epoxy, lactone, azlactone or isocyanato group, if the functional group of the chain transfer agent is, for example, an amino or hydroxy group; or are amino, hydroxy, if the functional group of the chain transfer agent is, for example, carboxy or the like.

One group of preferred reactive groups comprises carboxy, carboxylic acid anhydride, azlactone or isocyanato, in particular isocyanato. A suitable organic compound having such reactive group and an ethylenically unsaturated double bond is, for example, of formula

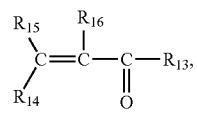
(4a)

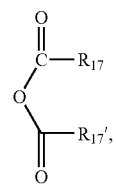
(4b)

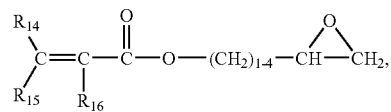
(4c)

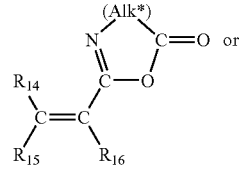
(4d)

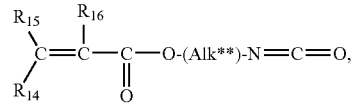
(4e)

wherein $R_{13}$ is halogen, hydroxy, unsubstituted or hydroxy-substituted $C_1$-$C_6$-alkoxy or phenoxy, $R_{14}$ and $R_{15}$ are each independently of the other hydrogen, $C_1$-$C_4$-alkyl, phenyl, carboxy or halogen, $R_{16}$ is hydrogen, $C_1$-$C_4$-alkyl or halogen, $R_{17}$ and $R_{17}'$ are each an ethylenically unsaturated radical having from 2 to 6 C-atoms, or $R_{17}$ and $R_{17}'$ together form a bivalent radical —C($R_{14}$)=C($R_{16}$)— wherein $R_{14}$ and $R_{16}$ are as defined above, and (Alk*) is $C_1$-$C_6$-alkylene, and (Alk**) is $C_2$-$C_{12}$-alkylene.

The following preferences apply to the variables contained in formulae (4a)-(4e):

$R_{13}$ is preferably halogen such as chlorine; hydroxy; or hydroxy-$C_1$-$C_4$-alkoxy, such as 2-hydroxyethyl; in particular chlorine;

One of the variables $R_{14}$ and $R_{15}$ is preferably hydrogen and the other one is hydrogen, methyl or carboxy. Most preferably $R_{14}$ and $R_{15}$ are each hydrogen;

$R_{16}$ is preferably hydrogen or methyl;

$R_{17}$ and $R_{17}'$ are preferably each vinyl or 1-methylvinyl, or $R_{17}$ and $R_{17}'$ together form a radical —C($R_{14}$)=C($R_{16}$)— wherein $R_{14}$ and $R_{16}$ are each independently hydrogen or methyl;

(Alk*) is preferably methylene, ethylene or 1,1-dimethyl-methylene, in particular a radical —CH$_2$— or —C(CH$_3$)$_2$—; and (Alk**) is preferably $C_2$-$C_4$-alkylene and in particular 1,2-ethylene.

Particularly preferred organic compounds having an ethylenically unsaturated double bond that are co-reactive to an amino or hydroxy group of the chain transfer agent are 2-isocyanatoethylmethacrylate (IEM), 2-vinyl-azlactone, 2-vinyl-4,4-dimethyl-azlactone, acrylic acid or a derivative thereof, for example acryloyl chloride or acrylic acid anhydride, methacrylic acid or a derivative thereof, for example methacryloyl chloride or methacrylic acid anhydride, maleic acid anhydride, 2-hydroxyethylacrylate (HEA), 2-hydroxymethacrylate (HEMA), glycidylacrylate or glycidylmethacrylat.

The reactions of a compound of formula (4a)-(4e) having a carboxylic acid halide group, carboxylic acid anhydride group, epoxy group, azlactone group or isocyanato group with an amino or hydroxy group of the copolymer formed in step (a) are well-known in the art and may be carried out as described in textbooks of organic chemistry. In general, the copolymer according to step (a) is reacted with stoichiometric amounts or preferably with an excess of the components of formula (4a)-(4e).

For example, the reaction of the carboxylic acid halide of formula (4a) with a hydroxy- or amino-group of the copolymer of step (a) can be carried out under the conditions that are customary for ester or amide formation, for example at temperatures of, for example, from −40 to 80° C., preferably from 0 to 50° C. and most preferably from 0 to 25° C., in a dipolar aprotic solvent, e.g. tetrahydrofuran, dioxane, DMSO or an $C_1$-$C_4$-alcanol, or in a mixture of water and one or more of the mentioned solvents, in the presence of a base, e.g. an alkali metal hydroxide, and, where applicable, in the presence of a buffer component such as hydrogen carbonate or a stabiliser. Suitable stabilisers are, for example, 2,6-dialkylphenols, hydroquinone derivatives, e.g. hydroquinone or hydroquinone monoalkyl ethers, or N-oxides, e.g. 4-hydroxy-2,2,6,6-tetramethyl-piperidin-1-yl. The reaction times may vary within wide limits, a period of, for example, from 5 minutes to 12 hours, preferably from 15 minutes to 6 hours and especially from 20 minutes to 3 hours, generally having been found practicable.

The reaction of a carboxylic acid anhydride or epoxide of formula (4b) or (4c) with a hydroxy- or amino-group of the copolymer of step (a) may be carried out as described in organic textbooks, for example in an acidic or in a basic medium.

The reaction of an azlactone of formula (4d) with a hydroxy- or amino-group of the polymer according to step (a) may be carried out at elevated temperature, for example at about 50 to 75° C., in a suitable organic solvent, for example an aprotic polar solvent such as DMF, DMSO, dioxane and the like, optionally in the presence of a catalyst, for example in the presence of a tertiary amine such as triethyl amine or an organotin salt such as dibutyltin dilaurate, or in particular in the presence of 1,8-diazabicyclo[5.4.0]undec-7-ene (DBU).

The reaction of a compound of formula (4e) with a hydroxy- or amino-group of the polymer according to step (a) can be carried out under the conditions that are customary for the formation of urethanes or ureas. In case of urethane formation it is advantageously to perform the reaction in an inert solvent. Amino-copolymers of step (a) may be reacted with the isocyanate of formula (4e) also in an aqueous medium.

Suitable inert solvents for the reaction of a copolymer of step (a) with a compound of formula (4e) are aprotic, preferably polar, solvents, for example hydrocarbons (petroleum ether, methylcyclohexane, benzene, toluene, xylene), halogenated hydrocarbons (chloroform, methylene chloride, trichloroethane, tetrachloroethane, chlorobenzene), ethers (diethyl ether, dibutyl ether, ethylene glycol dimethyl ether, diethylene glycol dimethyl ether, tetrahydrofuran, dioxane), ketones (acetone, dibutyl ketone, methyl ethyl ketone, methyl isobutyl ketone), carboxylic acid esters and lactones (ethyl acetate, butyrolactone, valerolactone), alkylated carboxylic acid amides (N,N-dimethylacetamide, N-methylpyrrolidone), nitriles (acetonitrile), sulfones and sulfoxides (dimethyl sulfoxide, tetramethylenesulfone). Polar solvents are preferably used. The reaction temperature may be, for example, from −40 to 200° C. When catalysts are used, the temperatures may advantageously be in the range of from 0 to 50° C., preferably at room temperature. Suitable catalysts are, for example, metal salts, such as ferric chloride or alkali metal salts of carboxylic acids, tertiary amines, for example ($C_1$-$C_6$alkyl)$_3$N (tri-ethylamine, tri-n-butylamine), N-methylpyrrolidine, N-methylmorpholine, N,N-dimethylpiperidine, pyridine and 1,4-diaza-bicyclooctane. Tin salts have been found to be especially effective, especially alkyltin salts of carboxylic acids, for example dibutyltin dilaurate and tin dioctoate. The isolation and purification of the compounds prepared is carried out according to known methods, for example by means of extraction, crystallisation, recrystallisation or chromatographic purification methods.

The compounds of the formula (4a), (4b), (4c), (4d) and (4e) are known compounds which are commercially available or may be prepared according to known methods.

Another group of suitable organic compounds having an ethylenically unsaturated double bond in step (b) are those having an amino, hydroxy or epoxy group that is coreactive to the carboxy group or a derivative thereof of the copolymer of step (a). Examples are allyl amine, allyl alcohol, 2-hydroethyl acrylate and methacrylate or preferably a compound of formula (9c) above, for example glycidyl acrylate or methacrylate The reaction may be carried out as described above for ester or amide formation.

Throughout the application terms such as carboxy, carboxylic acid, —COOH, sulfo, —SO$_3$H, amino, —NH$_2$ and the like always include the free acid or amine as well as a suitable salt thereof, for example a biomedically or in particular occularly acceptable salt thereof such as, for example, a sodium, potassium, ammonium salt or the like (of an acid), or a hydrohalide such a hydrochloride (of an amine).

The copolymers obtainable according to the invention are prepolymers and are therefore crosslinkable, but uncrosslinked or, at least, substantially uncrosslinked; in addition, they are stable, that is to say spontaneous crosslinking as a result of homopolymerisation does not take place. In particular, the amount of non-volatile extractables remaining after said work up operations is very low, so that the crosslinkable copolymers may be further processed to biomedical articles without additional time-consuming purification processes.

The prepolymers of the invention are crosslinkable in a controlled and extremely effective manner, especially by photo-crosslinking.

The present invention further relates, therefore, to a polymer that can be obtained by crosslinking thermally or, preferably, by photo-crosslinking a prepolymer obtainable by the above-described process, in the presence or, preferably, in the absence of an additional vinyl comonomer. These crosslinked polymers are water-insoluble.

In the photo-crosslinking, a photoinitiator capable of initiating free-radical crosslinking is suitably added. Examples thereof will be familiar to the person skilled in the art, suitable photoinitiators that may specifically be mentioned being benzoin methyl ether, 1-hydroxy-cyclohexylphenyl ketone, Darocure® 1173 or 2959 or Irgacure® types. The crosslinking can then be brought about by actinic radiation, e.g. visible light, UV light, or ionising radiation, e.g. gamma rays or X-rays. The amount of photoinitiator may be selected within wide limits, an amount of from 0.01 to 1.5% by weight and especially of from 0.05 to 0.5% by weight, based in each case of the prepolymer contents, having proved beneficial.

The crosslinkable prepolymer of the invention is introduced into the crosslinking process preferably in pure form, particularly substantially free from undesired constituents, such as, for example, free from monomeric, oligomeric or polymeric starting compounds used for the preparation of the prepolymer, and/or free from secondary products formed during the preparation of the prepolymer. Said prepolymers in pure form are obtained advantageously by previously purifying them in a manner known per se, for example by precipitation with a suitable solvent, filtration and washing, extraction in a suitable solvent, dialysis, reverse osmoses (RO) or ultrafiltration, reverse osmoses and ultrafiltration being especially preferred.

The preferred purification processes for the prepolymers of the invention, reverse osmoses and ultrafiltration, can be carried out in a manner known per se. It is possible for the ultrafiltration and reverse osmoses to be carried out repeatedly, for example from two to ten times. Alternatively, the ultrafiltration and reverse osmoses can be carried out continuously until the selected degree of purity is attained. The selected degree of purity can in principle be as high as desired. In particular, it has turned out that the crosslinkable copolymers of the present invention, due to their specific chemical composition, comprise a very low amount of non-volatile extractables, that are undesired by-products which are not removable by said work-up processes but may leach out over time; due to this the crosslinkable copolymers of the present invention may be further processed to biomedical articles without additional time-consuming purification processes of said biomedical articles being necessary.

The prepolymers of the invention may be crosslinked conveniently in form of a solution. The solution used for crosslinking is preferably an aqueous solution or a solution comprising one or more different organic solvents. Suitable organic solvents are in principle all solvents that dissolve the polymers according to the invention and an optional vinyl comonomer which may be additionally used, e.g. alcohols, such as $C_1$-$C_6$— alkanols, e.g. n- or iso-propanol, ethanol or methanol, glycols such as ethylene glycol, diethylene glycol, propylene glycol, butylene glycol, carboxylic acid amides, such as dimethylformamide, or dimethyl sulfoxide, and mixtures of suitable solvents, e.g. mixtures of water with an alcohol, e.g. a water/propanol, water/ethanol or a water/methanol mixture, or mixtures of water with a glycol.

It must be understood that a solution containing a prepolymer of the invention for making lenses can also comprise various components, such as, for example, polymerization initiators (e.g., photoinitiator or thermal initiator), a visibility tinting agent (e.g., dyes, pigments, or mixtures thereof), UV-blocking (absorbing) agent, photosensitizers, inhibitors, antimicrobial agents (e.g., preferably silver nanoparticles or stabilized silver nanoparticles), bioactive agent, leachable lubricants, fillers, and the like, as known to a person skilled in the art.

Initiators, for example, selected from materials well known for such use in the polymerization art, may be included in the lens-forming material in order to promote, and/or increase the rate of, the polymerization reaction. An initiator is a chemical agent capable of initiating polymerization reactions. The initiator can be a photoinitiator or a thermal initiator.

Examples of preferred pigments include any colorant permitted in medical devices and approved by the FDA, such as D&C Blue No. 6, D&C Green No. 6, D&C Violet No. 2, carbazole violet, certain copper complexes, certain chromium oxides, various iron oxides, phthalocyanine green, phthalocyanine blue, titanium dioxides, etc. See Marmiom DM Handbook of U.S. Colorants for a list of colorants that may be used with the present invention. A more preferred embodiment of a pigment include (C.I. is the color index no.), without limitation, for a blue color, phthalocyanine blue (pigment blue 15:3, C.I. 74160), cobalt blue (pigment blue 36, C.I. 77343), Toner cyan BG (Clariant), Permajet blue B2G (Clariant); for a green color, phthalocyanine green (Pigment green 7, C.I. 74260) and chromium sesquioxide; for yellow, red, brown and black colors, various iron oxides; PR122, PY154, for violet, carbazole violet; for black, Monolith black C-K (CIBA Specialty Chemicals).

The bioactive agent incorporated in the polymeric matrix is any compound that can prevent a malady in the eye or reduce the symptoms of an eye malady. The bioactive agent can be a drug, an amino acid (e.g., taurine, glycine, etc.), a polypeptide, a protein, a nucleic acid, or any combination thereof. Examples of drugs useful herein include, but are not limited to, rebamipide, ketotifen, olaptidine, cromoglycolate, cyclosporine, nedocromil, levocabastine, lodoxamide, ketotifen, or the pharmaceutically acceptable salt or ester thereof. Other examples of bioactive agents include 2-pyrrolidone-5-carboxylic acid (PCA), alpha hydroxyl acids (e.g., glycolic, lactic, malic, tartaric, mandelic and citric acids and salts thereof, etc.), linoleic and gamma linoleic acids, and vitamins (e.g., B5, A, B6, etc.).

Examples of leachable lubricants include without limitation mucin-like materials and non-crosslinkable hydrophilic polymers (i.e., without ethylenically unsaturated groups). Exemplary mucin-like materials include without limitation polyglycolic acid, polylactides, collagen, hyaluronic acid, and gelatin.

Any hydrophilic polymers or copolymers without any ethylenically unsaturated groups can be used as leachable lubricants. Preferred examples of non-crosslinkable hydrophilic polymers include, but are not limited to, polyvinyl alcohols (PVAs), polyamides, polyimides, polylactone, a homopolymer of a vinyl lactam, a copolymer of at least one vinyl lactam in the presence or in the absence of one or more hydrophilic vinylic comonomers, a homopolymer of acrylamide or methacrylamide, a copolymer of acrylamide or methacrylamide with one or more hydrophilic vinylic monomers, polyethylene oxide (i.e., polyethylene glycol (PEG)), a polyoxyethylene derivative, poly-N—N-dimethylacrylamide, polyacrylic acid, poly 2 ethyl oxazoline, heparin polysaccharides, polysaccharides, and mixtures thereof.

The number-average molecular weight $M_n$ of the non-crosslinkable hydrophilic polymer is preferably from 20,000 to 500,000, more preferably from 30,000 to 100,000, even more preferably from 35,000 to 70,000.

According to this embodiment of the invention, the photo-crosslinking is preferably effected from a solution comprising (i) one or more crosslinkable copolymers according to the invention which can be obtained as a result of the preferred purification step, ultrafiltration, (ii) one or more solvents selected from the group consisting of a $C_1$-$C_6$— alkanol, a glycol, a carboxylic acid amide, dimethyl sulfoxide and water, and optionally (iii) an additional vinyl comonomer. For example, photo-crosslinking of the prepolymers is carried out in water, in ethanol or n- or iso-propanol, or in a mixture of water and ethanol or n- or iso-propanol.

The vinyl comonomer that can additionally be used according to the invention in the photo-crosslinking may be hydrophilic or hydrophobic or may be a mixture of a hydrophobic and a hydrophilic vinyl monomer. Suitable vinyl monomers include especially those which are customarily used in the manufacture of contact lenses. The expression "hydrophilic vinyl monomer" is understood to mean a monomer that typically produces as homopolymer a polymer that is water-soluble or capable of absorbing at least 10% by weight water. Analogously, the expression "hydrophobic vinyl monomer" is understood to mean a monomer that typically produces as homopolymer a polymer that is water-insoluble or capable of absorbing less than 10% by weight water.

The proportion of vinyl comonomers, if used, is preferably from 5 to 60% by weight, especially from 10 to 30% by weight, of vinyl comonomer relative to the weight of prepolymers of the invention.

It is also preferred to use a hydrophobic vinyl comonomer or a mixture of a hydrophobic vinyl comonomer with a hydrophilic vinyl comonomer, the mixture containing at least 50% by weight of a hydrophobic vinyl comonomer. In that manner, the mechanical properties of the polymer can be improved without the water content being appreciably reduced. In principle, however, both conventional hydrophobic vinyl comonomers and conventional hydrophilic vinyl comonomers are suitable for copolymerisation with a prepolymer of the invention.

Suitable hydrophobic vinyl comonomers include, without the following being an exhaustive list, $C_1$-$C_{18}$alkyl acrylates and methacrylates, $C_3$-$C_{18}$alkylacrylamides and -meth-acrylamides, acrylonitrile, methacrylonitrile, vinyl-$C_1$-$C_{18}$alkanoates, $C_2$-$C_{18}$alkenes, $C_2$-$C_{18}$haloalkenes, styrene, $C_1$-$C_6$alkylstyrene, vinyl alkyl ethers in which the alkyl moiety has from 1 to 6 carbon atoms, $C_2$-$C_{10}$ perfluoroalkyl acrylates and methacrylates or correspondingly partially fluorinated acrylates and methacrylates, $C_3$-$C_{12}$ perfluoroalkyl-ethyl-thiocarbonylaminoethyl acrylates and methacrylates, acryloxy- and methacryloxy-alkylsiloxanes, N-vinylcarbazole, $C_1$-$C_{12}$alkyl esters of maleic acid, fumaric acid, itaconic acid, mesaconic acid and the like. Preferred are, for example, $C_1$-$C_4$alkyl esters of vinylically unsaturated carboxylic acids having from 3 to 5 carbon atoms or vinyl esters of carboxylic acids having up to 5 carbon atoms.

Examples of suitable hydrophobic vinyl comonomers include methyl acrylate, ethyl acrylate, propyl acrylate, isopropyl acrylate, cyclohexyl acrylate, 2-ethylhexyl acrylate, methyl meth-acrylate, ethyl methacrylate, propyl methacrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyltoluene, vinyl ethyl ether, perfluorohexylethylthiocarbonylaminoethyl methacrylate, isobornyl methacrylate, trifluoroethyl methacrylate, hexa-fluoroisopropyl methacrylate, hexafluorobutyl methacrylate, tris-trimethylsilyloxy-silyl-propyl methacrylate, 3-methacryloxypropylpentamethyldisiloxane and bis(methacryloxypropyl)-tetramethyldisiloxane.

Suitable hydrophilic vinyl comonomers include, without the following being an exhaustive list, hydroxy-substituted lower alkyl acrylates and methacrylates, acrylamide, methacrylamide, lower alkylacrylamide and -methacrylamide, ethoxylated acrylates and methacrylates, hydroxy-substituted lower alkylacrylamides and methacrylamides, hydroxy-substituted lower alkyl vinyl ethers, sodium ethylenesulfonate, sodium styrenesulfonate, 2-acrylamido-2-methylpropanesulfonic acid, N-vinylpyrrole, N-vinylsuccinimide, N-vinylpyrrolidone, 2- or 4-vinylpyridine, acrylic acid, methacrylic acid, amino- (the term "amino" also including quaternary ammonium), mono-lower alkylamino- or di-lower alkylamino-lower alkyl acrylates and methacrylates, allyl alcohol and the like. Preferred are, for example, hydroxy-substituted $C_2$-$C_4$alkyl (meth)acrylates, five- to seven-membered N-vinyl lactams, N,N-di-$C_1$-$C_4$alkyl(meth)-acrylamides and vinylically unsaturated carboxylic acids having a total of from 3 to 5 carbon atoms.

Examples of suitable hydrophilic vinyl comonomers include hydroxyethyl methacrylate, hydroxyethyl acrylate, acrylamide, methacrylamide, dimethylacrylamide, allyl alcohol, vinyl-pyridine, vinylpyrrolidine, glycerol methacrylate, N-(1,1-dimethyl-3-oxobutyl)-acrylamide and the like.

Preferred hydrophobic vinyl comonomers are methyl methacrylate and vinyl acetate. Preferred hydrophilic vinyl comonomers are 2-hydroxyethyl methacylate, N-vinylpyrrolidone and acrylamide. Most preferably, the crosslinking of the prepolymers of the invention is carried out in the absence of a vinylic comonomer.

The solution comprising a prepolymer of the invention may be processed in a manner known per se to form moldings, especially ophthalmic moldings such as contact lenses, for example by carrying out the photo-crosslinking of the prepolymers of the invention in a suitable mold, in particular a contact lens mold. For example, the solution is introduced into an opthalmic mold in a manner known per se, such as, especially, by conventional metering in, for example by dropwise introduction. Suitable molds are generally customary contact lens molds as known in the state of the art. Thus, the contact lenses according to the invention can be manufactured, for example, in a manner known per se, for example in a conventional "spin-casting mold", as described, for example, in U.S. Pat. No. 3,408,429, or by the so-called Full-Mold process in a static mold, as described, for example, in U.S. Pat. No. 4,347,198. Appropriate molds may be, for example, plastic molds, for example those made of polypropylene, polystyrene, Topas, or the like, or glass molds, for example those made of Quartz, sapphire glass or other kinds of glass. The use of re-usable molds is preferred.

The crosslinking can be triggered in the mold, for example by actinic radiation, such as, for example, visible light or UV light, or by ionising radiation, such as, for example, gamma radiation, electron radiation or X radiation. The crosslinking can where appropriate also be triggered thermally or electrochemically. Attention is drawn to the fact that the photo-crosslinking can be carried out in a very short time, for example in $\leq$30 minutes, preferably $\leq$20 minutes, more preferably $\leq$5 minutes, even more preferably in $\leq$1 minute, especially in 10 to 45 seconds, especially preferably, as disclosed in the examples.

The opening of the mold such that the molding can be removed from the mold can be carried out in a manner known per se.

If the molding manufactured according to the invention is a contact lens and the latter has been manufactured from a previously purified prepolymer of the invention, then it is normally unnecessary for the removal of the molding to be followed by purification steps, e.g. extraction, because the prepolymers used do not contain any undesired low-molecular-weight constituents; consequently, the crosslinked product also is free or substantially free of such constituents and subsequent extraction can be dispensed with. The contact lens can accordingly be converted into a ready-for-use contact lens directly in conventional manner by solvent-exchange and hydration. Suitable forms of hydration capable of producing ready-for-use contact lenses with a wide variety of water contents are known to the person skilled in the art. The contact lens is swollen, for example, in water, in an aqueous salt solution, especially in an aqueous salt solution having an osmolarity of approximately from 200 to 450 milliosmol in 1000 ml (unit: mosm/l), preferably approximately from 250 to 350 mosm/l and especially approximately 300 mosm/l, or in a mixture of water or an aqueous salt solution with a physiologically tolerable polar organic solvent, for example glycerol. Swelling of the prepolymer in water or in aqueous salt solutions is preferred.

The aqueous salt solutions used for the hydration are advantageously solutions of physiologically tolerable salts, such as buffer salts customary in the field of contact lens care, e.g. phosphate salts, or isotonising agents customary in the field of contact lens care, such as, especially, alkali metal halides, e.g. sodium chloride, or solutions of mixtures thereof. An example of an especially suitable salt solution is a synthetic, preferably buffered, lachrymal fluid that has been matched to natural lachrymal fluid with regard to pH value and osmolarity, e.g. an unbuffered or preferably buffered, for example phosphate buffer-buffered, sodium chloride solution the osmolarity and pH value of which correspond to the osmolarity and pH value of human lachrymal fluid.

The hydration fluids defined above are preferably pure, that is to say free or substantially free of undesired constituents. Most preferably, the hydration fluid is pure water or a synthetic lachrymal fluid as described above.

If the molding manufactured according to the invention is a contact lens and the latter has been manufactured from an aqueous solution or mesophase of a previously purified prepolymer of the invention, the crosslinked product also will not contain any troublesome impurities. There is normally no need, therefore, for subsequent extraction. Since the crosslinking is carried out in an aqueous medium, there is also no need for subsequent hydration. In accordance with an advantageous embodiment, therefore, the contact lenses obtainable by this process are distinguished by the fact that they are suitable for use as intended without extraction or hydration. The expression "use as intended" is understood in this context to mean especially that the contact lenses can be inserted into the human eye.

The prepolymers of the invention are especially suitable for the manufacture of mass-produced articles, such as, for example, contact lenses that are worn for a short time, for example for a month, a week or just one day, and are then replaced by new lenses. This is especially true if the contact lenses are prepared from an aqueous solution of a copolymer of the invention which can be used on the eye without subsequent treatment steps, such as extraction or hydration.

The invention further relates to moldings that comprise or, preferably, substantially consist of a crosslinked prepolymer of the invention. Further examples of moldings of the invention, apart from contact lenses, are biomedical or special ophthalmic moldings, e.g. intraocular lenses, artificial cornea, eye bandages, wound healing dressings, materials for the sustained release of an active compound such as a drug delivery patch, moldings for use in surgery, such as heart valves, vascular grafts, catheters, artificial organs, encapsulated biologic implants, e.g. pancreatic islets, materials for prostheses such as bone substitutes and the like, moldings for diagnostics, biomedical instruments, and films or membranes, e.g. membranes for controlling diffusion, photo-structurable films for information storage, or photoresist materials, e.g. membranes or moldings for etch resists or screen print resists.

Biomedical moldings, especially ophthalmic moldings such as contact lenses obtainable according to the invention have a range of unusual and extremely advantageous properties. Among those properties, there may be mentioned, for example, their excellent compatibility with the human cornea, which is due to a balanced ratio of water content, oxygen permeability and mechanical properties. The contact lenses of the invention furthermore have a high dimensional stability. Even after autoclaving at, for example, approximately 120° C. no changes in shape can be detected.

Moldings obtainable from the prepolymers of the invention are preferably at least partly bicontinuous, that is to say the moldings have at least two partly bicontinuous phases, in particular an oxygen-permeable and an ion-permeable phase, which are intermingled. Owing to this structural feature, contact lenses and other biomedical articles obtainable from said prepolymers have a range of unusual and extremely advantageous properties and are therefore suited to extended periods of wear (true extended wear, i.e., seven days or more). Among these properties are, for example, their excellent compatibility with the human cornea and with tear fluid, if necessary after suitable surface treatment (e.g. coating), which is based on a balanced ratio between water content, oxygen permeability, ion permeability and mechanical and absorptive properties. This results in high comfort and the absence of irritation and allergenic effects. Owing to their favorable permeability properties with respect to gases ($CO_2$ and $O_2$), various salts, nutrients, water and diverse other components of tear fluid, the contact lenses prepared according to the process of the invention have no effect, or virtually no effect, on the natural metabolic processes in the cornea. Furthermore, the contact lenses obtainable according to the process are optical clear and transparent, have a high shelf life and good mechanical properties, for example concerning the modulus of elasticity, elongation at break or dimensional stability.

The molded contact lenses can further subject to further processes, such as, for example, surface treatment, sterilization, and the like.

A contact lens of the invention has an oxygen permeability of preferably at least about 40 barrers, more preferably at least about 60 barrers, even more preferably at least about 80 barrers; and an elastic modulus of about 1.5 MPa or less, preferably about 1.2 MPa or less, more preferably about 1.0 MPa or less. In accordance with the invention, an oxygen permeability is an apparent (directly measured when testing a sample with a thickness of about 100 microns) oxygen permeability according to procedures described in Examples.

A contact lens of the invention further has an Ionoflux Diffusion Coefficient, D, of, preferably at least about $1.5 \times 10^{-6}$ mm$^2$/min, more preferably at least about $2.6 \times 10^{-6}$ mm$^2$/min, even more preferably at least about $6.4 \times 10^{-6}$ mm$^2$/min.

A contact lens of the invention further has a water content of preferably from about 15% to about 55%, more preferably from about 20% to about 38% by weight when fully hydrated. The water content of a silicone hydrogel contact lens can be measured according to Bulk Technique as disclosed in U.S. Pat. No. 5,849,811.

In the Examples which follow, amounts are by weight, unless specified otherwise, and temperatures are given in degrees Celsius.

Example 1

Preparation of a PDMS Crosslinker

In a 4-L beaker, 24.13 g of $Na_2CO_3$, 80 g of NaCl and 1.52 kg of deionized water are mixed to dissolve. In a separate 4-L beaker, 700 g of bis-3-aminopropyl-polydimethylsiloxane (Shin-Etsu, MW ca. 11500) are dissolved in 1000 g of hexane. A 4-L reactor is equipped with overhead stirring with turbine agitator and a 250-mL addition funnel with micro-flow controller. The two solutions are then charged to the reactor, and mixed for 15 minutes with heavy agitation to produce an emulsion. 14.5 g of acryloyl chloride are dissolved in 100 mL of hexane and charged to the addition funnel. The acryloyl chloride solution is added dropwise to the emulsion under heavy agitation over one hour. The emulsion is stirred for 30 minutes on completion of the addition and then agitation is stopped and the phases are allowed to separate overnight. The aqueous phase is decanted and the organic phase is washed twice with a mixture of 2.0 kg of 2.5% NaCl dissolved in water. The organic phase is then dried over magnesium sulfate, filtered to 1.0 μm exclusion, and concentrated on a rotary evaporator. The resulting oil is further purified by high-vacuum drying to constant weight. Analysis of the resulting product by titration reveals 0.175 mEq/g of C=C double bonds.

Example 2

Preparation of a PDMS Crosslinker

In a 4-L beaker, 61.73 g of $Na_2CO_3$, 80 g of NaCl and 1.52 kg of deionized water are mixed to dissolve. In a separate 4-L beaker, 700 g of bis-3-aminopropyl-polydimethylsiloaxane (Shin-Etsu, MW ca. 4500) are dissolved in 1000 g of hexane. A 4-L reactor is equipped with overhead stirring with turbine agitator and a 250-mL addition funnel with micro-flow controller. The two solutions are then charged to the reactor, and mixed for 15 minutes with heavy agitation to produce an emulsion. 36.6 g of acryloyl chloride is dissolved in 100 mL of hexane and charged to the addition funnel. The acryloyl chloride solution is added dropwise to the emulsion under heavy agitation over one hour. The emulsion is stirred for 30 minutes on completion of the addition and then agitation is stopped and the phases are allowed to separate overnight. The aqueous phase is decanted and the organic phase is washed twice with a mixture of 2.0 kg of 2.5% NaCl dissolved in water. The organic phase is then dried over magnesium sulfate, filtered to 1.0 μm exclusion, and concentrated on a rotary evaporator. The resulting oil is further purified by high-vacuum drying to constant weight. Analysis of the resulting product by titration reveals 0.435 mEq/g of C=C double bonds.

Example 3

Comparative Example

A. Preparation of the Crosslinkable Copolymer

A 2-L jacketed reactor is equipped with a heating/chilling loop, septum inlet adapter, reflux condenser with $N_2$-inlet adapter, and overhead stirring. A solution is generated by dissolving 48.76 g of the PDMS crosslinker produced by the procedure described in Example 1 and 17.71 g of PDMS crosslinker produced by the procedure described in Example 2 in 150 g of 1-propanol. This solution is charged to the reactor and cooled to 8° C. The solution is degassed by evacuating to less than 5 mBar, holding at vacuum for 15 minutes, and then re-pressurizing with dry nitrogen. This degas procedure is repeated for a total of 5 times.

In a separate 500 mL flask equipped with magnetic stirring and a vacuum-inlet adapter with valve, 1.93 g of cysteamine hydrochloride are dissolved in 300 mL of 1-propanol. In another 500 mL flask equipped with magnetic stirring and vacuum-inlet adapter with valve, a solution of 31.27 g of N,N-dimethylacrylamide (DMA) is dissolved in 300 mL of 1-propanol. In a third flask, similarly equipped, 0.35 g of azo-bis(isobutyronitrile) (AIBN) are dissolved in 150 g of 1-propanol. All three solutions are degassed twice by evacuation to 60 mBar, holding vacuum for 5 minutes, and then re-pressurizing with nitrogen.

Under a positive flow of nitrogen, the reactor is opened and the cysteamine hydrochloride, DMA, and AIBN solutions are charged to the reactor. Still holding at 8° C., the reactor is degassed by evacuating to less than 5 mBar and holding for 5 minutes, then re-pressurizing with nitrogen. A total of four degassing cycles are performed. The reactor is then heated to 68° C. and held at temperature under nitrogen with stirring for 16 hours. The reaction mixture is then transferred to a flask and vacuum stripped at 40° C./100 mBar on a rotary evaporator to remove 1-propanol. After the first 500 g of 1-propanol are removed, 500 g of water are added slowly with stirring to create an emulsion. The emulsion is then further stripped of 1-propanol until 200 g of distillate are collected. 200 g of water are again added back to the emulsion, and solvent-exchange is continued to collect a final 200 g of distillate. The emulsion is then diluted to 2.0 kg.

This emulsion is then charged to a 2-L reactor equipped with overhead stirring, refrigeration loop, thermometer, and the pH meter and dispensing tip of a Metrohm Model 718 STAT Titrino. The reaction mixture is then cooled to 1° C. 1.5 g of $NaHCO_3$ are charged to the emulsion and stirred to dissolve. The Titrino is set to maintain pH at 9.5 by intermittent addition of 15% sodium hydroxide solution. 6.2 mL of acryloyl chloride are then added over one hour using a syringe pump. The emulsion is stirred for another hour, then the Titrino is set to neutralize the reaction mixture by addition of a 15% solution of hydrochloric acid. The emulsion is then drained from the reactor, diluted to 3.5 L and filtered to 16 μm exclusion. The emulsion is purified by diafiltration (nominal molecular weight cut-off, 10,000D) with deionized water until the permeate conductance is below 2.5 μS/cm, and the polymer is isolated by lyophilization.

B. Preparation of Contact Lenses 18.83 g of the polymer obtained according to step A. above are dissolved in approximately 200 mL of 1-propanol, concentrated to ca. 70 g total solution weight, and filtered to 0.45 μm exclusion. 67.94 g of solution at 26.53% solids are recovered. 4.503 g of a 1% solution of 2-hydroxy-4'-hydroxyethyl-2-methylpropiophenone (IRGACURE®-2959, Ciba Specialty Chemicals) are added, and then the solution is concentrated to a final weight of 25.74 g (70.0% solids).

200 mg of the formulation are dosed into poly(propylene) contact lens molds and the molds are closed. The molds are then irradiated for 15 s with an ultraviolet light source having an intensity of 2.18 mW/cm². The molds are then opened, and the mold halves which have a lens attached are soaked in a mixture of 80% isopropanol, 20% water (v/v) overnight. The lenses are rinsed off the molds with this solvent mixture, then rinsed twice for 2 hrs. each in fresh aliquots of isopropanol/water mixture. The lenses are drained and then hydrated by immersion in deionized water. They are then rinsed three times for 2 h in pure water (3.0 mL/lens).

C. Measurement of Non-Volatile Extractables (NVE)

40 lenses, which are cast-molded in molds, removed from the molds, and are not subject to extraction, are then dried under vacuum (0.1 mBar) at room temperature for 16 hours. The lenses are then transferred to tared tins. Dry lens weight is determined as initial lens weight and the lenses are transferred to a jar, and 25 ml of isopropanol or methanol are added. The samples are put on a shaker (e.g., a rotary plate) for approximately 16 hours at room temperature. The lenses are rinsed twice with fresh isopropanol or methanol and then transferred to tared tins and dried in oven at 50° C. and <10 mBar vacuum for approximately 16 hours. The tins are then removed from the vacuum oven and the weight of the lenses is measured (final lens weight). The value "% NVE" quoted is $$\frac{\text{initial lens weight} - \text{final lens weight}}{\text{initial lens weight}},$$

expressed as a percentage value.

Example 4

A. Preparation of the Crosslinkable Copolymer

A 2-L jacketed reactor is equipped with a heating/chilling loop, septum inlet adapter, reflux condenser with $N_2$-inlet adapter, and overhead stirring. A solution is generated by dissolving 48.76 g of PDMS crosslinker produced by the procedure described in Example 1 and 17.71 g of PDMS crosslinker produced by the procedure described in Example 2 in 150 g of 1-propanol. This solution is charged to the reactor and cooled to 8° C. The solution is degassed by evacuating to less than 5 mBar, holding at vacuum for 15 minutes, and then re-pressurizing with dry nitrogen. This degas procedure is repeated for a total of 5 times.

In a separate 500 mL flask equipped with magnetic stirring and a vacuum-inlet adapter with valve, 1.93 g of cysteamine hydrochloride are dissolved in 300 mL of 1-propanol. In another 500 mL flask equipped with magnetic stirring and vacuum-inlet adapter with valve, a solution of 36.63 g of hydroxyethyl acrylate (HEA) and 2.14 g of acrylic acid (AA) are dissolved in 300 mL of 1-propanol. In a third flask, similarly equipped, 0.35 g of AIBN are dissolved in 150 g of 1-propanol. All three solutions are degassed twice by evacuation to 60 mBar, holding vacuum for 5 minutes, and then re-pressurizing with nitrogen.

Under a positive flow of nitrogen, the reactor is opened and the cysteamine hydrochloride, HEA/AA, and AIBN solutions are charged to the reactor. Still holding at 8° C., the reactor is degassed by evacuating to less than 5 mBar and holding for 5 minutes, then re-pressurizing with nitrogen. A total of four degassing cycles are performed. The reactor is then heated to 68° C. and held at this temperature under nitrogen with stirring for 16 hours. The reaction mixture is then solvent exchanged to water according to the procedure described in Example 3. The resulting emulsion ios then diluted to 2.0 kg.

This emulsion is then acrylated with 6.2 mL of acryloyl chloride by the procedure described in Example 3. The emulsion is then drained from the reactor, diluted to 3.5 L and filtered to 16 µm exclusion. The emulsion is purified by diafiltration (nominal molecular weight cut-off, 10,000D) with deionized water until the permeate conductance was below 2.5 µS/cm, and the polymer is isolated by lyophilization.

B. Preparation of Contact Lenses 15.73 g of the polymer from step A. are dissolved in approximately 320 mL of 1-propanol, then dried with 1.5 g of magnesium sulfate and filtered to 17 µm exclusion using a fritted glass filter. 312.25 g of solution at 4.61% solids are recovered. 3.61 g of a 1% solution of 2-hydroxy-4'-hydroxyethyl-2-methylpropiophenone (IRGACURE®-2959, Ciba Specialty Chemicals) are added, and then the solution is concentrated to a final weight of 20.57 g (70% solids).

The above formulation is used to cast lenses as follows. 200 mg of the formulation are dosed into poly(propylene) molds and the molds are closed. The molds are then irradiated for 18 with an ultraviolet light source having an intensity of 2.01 mW/cm². The molds are then opened, and the lenses are deblocked and rinsed by the procedure of Example 3. 40 lenses are then subjected to the determination of % NVE as described in Example 3.

Example 5

A. Preparation of the Crosslinkable Copolymer

A 2-L jacketed reactor is equipped with a heating/chilling loop, septum inlet adapter, reflux condenser with $N_2$-inlet adapter, and overhead stirring. A solution is generated by dissolving 48.76 g of PDMS crosslinker produced by the procedure described in Example 1 and 17.71 g of PDMS crosslinker produced by the procedure described in Example 2 in 150 g of 1-propanol. This solution was charged to the reactor and cooled to 8° C. The solution is degassed by evacuating to less than 5 mBar, holding at vacuum for 15 minutes, and then re-pressurizing with dry nitrogen. This degas procedure is repeated for a total of 5 times.

In a separate 500 mL flask equipped with magnetic stirring and a vacuum-inlet adapter with valve, 1.93 g of cysteamine hydrochlorideare dissolved in 300 mL of 1-propanol. In another 500 mL flask equipped with magnetic stirring and vacuum-inlet adapter with valve, a solution of 36.63 g of HEA and 3.06 g of M are dissolved in 300 mL of 1-propanol. In a third flask, similarly equipped, 0.35 g of AIBN are dissolved in 150 g of 1-propanol. All three solutions are degassed twice by evacuation to 60 mBar, holding vacuum for 5 minutes, and then re-pressurizing with nitrogen.

Under a positive flow of nitrogen, the reactor is opened and the cysteamine hydrochloride, HEA/A, and AIBN solutions are charged to the reactor. Still holding at 8° C., the reactor is degassed by evacuating to less than 5 mBar and holding for 5 minutes, then re-pressurizing with nitrogen. A total of four degassing cycles are performed. The reactor is then heated to 68° C. and held at temperature under nitrogen with stirring for 16 hours. The reaction mixture is then solvent exchanged to water according to the procedure described in Example 3. The resulting emulsion is then diluted to 2.0 kg.

This emulsion is then acrylated with 6.2 mL of acryloyl chloride by the procedure described in Example 3. The emulsion is then drained from the reactor, diluted to 3.5 L and filtered to 16 µm exclusion. The emulsion is purified by diafiltration (nominal molecular weight cut-off, 10,000D) with deionized water until the permeate conductance is below 2.5 µS/cm, and polymer is isolated by lyophilization.

B. Preparation of Contact Lenses 18.59 g of polymer from step A. are dissolved in approximately 200 mL of 1-propanol, then dried with 1.5 g of magnesium sulfate and filtered to 17 µm exclusion using a fritted glass filter. 154.5 g of solution at 10.26% solids are recovered. 3.96 g of a 1% solution of 2-hydroxy-4'-hydroxyethyl-2-methylpropiophenone (IRGACURE®-2959, Ciba Specialty Chemicals) are added, and then the solution is concentrated to a final weight of 22.64 g (70% solids).

The above formulation is used to cast lenses as follows. 200 mg of the formulation are dosed into poly(propylene) molds and the molds are closed. The molds are then irradiated for 23 with an ultraviolet light source having an intensity of 1.6 mW/cm². The molds are then opened, and the lenses are deblocked and rinsed by the procedure of Example 3. 40 lenses are then subjected to the determination of % NVE as described in Example 3.

Table 1 lists the characteristics of the lenses produced in Examples 3, 4 and 5:

| Example | Elongation to Break | E' Modulus | % NVE (IPA) |
|---|---|---|---|
| Example 3 (Prior Art) | 330% | 0.48 MPa | 24% |
| Example 4 | 265% | 0.74 MPa | 13% |
| Example 5 | 220% | 0.70 MPa | 5.8% |

As can be seen from the table, there is a large, unexpected positive advantage arising simply from substituting equimolar amounts of other monomers, such as acrylic acid or hydroxyethyl acrylate, for N,N-dimethylacrylamide in the prior art. Lower extractables can be achieved without substantial loss of lens toughness or flexibility.

Example 6

A. Preparation of the Crosslinkable Copolymer

A 2-L jacketed reactor is equipped with a heating/chilling loop, reflux condenser, N₂-inlet/vacuum adapter, feeding tube adapter and overhead mechanical stirring. A solution is generated by dissolving 90.00 g of PDMS crosslinker produced by the procedure described in Example 1 and 30.00 g of PDMS crosslinker produced by the procedure described in Example 2 in 480 g of 1-propanol. This solution is charged to the reactor and cooled to 8° C. The solution is degassed by evacuating to less than 15 mBar, holding at vacuum for 15 minutes, and then re-pressurizing with dry nitrogen. This degas procedure is repeated for a total of 3 times. The reactor is held under a blanket of dry nitrogen.

In a separate flask, a monomer solution is prepared by mixing 1.50 g of cysteamine hydrochloride, 0.3 g of AIBN, 55.275 g of DMA, 18.43 g of HEA and 364.5 g of 1-propanol in the same manner as described in Example 4. This solution is filtered with a Waterman 540 filter paper, and then added to the reactor through a degas unit and HPLC pump with a flow rate of 3.0 mL/minute. The reaction temperature is then elevated to 68° C. with a heating ramp about one hour.

In a second flask, a feeding solution is prepared by mixing 4.5 g of cysteamine hydrochloride and 395.5 g of 1-propanol and then filtering with Waterman 540 filter paper. When the reactor temperature reaches 68° C., this solution is slowly dosed into the reactor through the degasser/HPLC pump over 3 hours. The reaction is then continued at 68° C. for an additional 3 hours, on which heating has discontinued and the reactor is allowed to cool to room temperature.

The reaction mixture is transferred to a flask and stripped solvent at 40° C. under vacuum on a rotary evaporator until 1000 g of sample remained. The solution is then slowly mixed with 2000 g of deionized water with rapid agitation. Additional solvent is further removed until about 2000 g of sample remain. During this stripping process, the solution gradually becomes an emulsion. The resulting material is purified by ultrafiltration over a 10 kD molecular weight cut-off membrane until the permeate conductance is below 2.5 µS/cm.

The purified copolymer solution is acrylated in the same manner as described in Example 3 except that 7.99 g of NaHCO₃ and 11.59 mL of acryloyl chloride are used for the reaction. The product is purified by ultrafiltration again with 10 kD molecular weight cut-off membrane until the permeate conductance is below 2.5 µS/cm. The final macromonomer is isolated by lyophilization.

B. Preparation of Contact Lenses

The macromonomer from step A. is formulated in the same manner as described in Example 3 except that the solution is concentrated to a final weight corresponding to 65.0% solids content.

The above formulation is used to cast lenses and to determine the extractables by the process of Example 3.

Example 7

A. Preparation of the Crosslinkable Copolymer

A 2-L jacketed reactor is equipped with a heating/chilling loop, reflux condenser, N₂-inlet/vacuum adapter, feeding tube adapter and overhead mechanical stirring. A solution is generated by dissolving 60.00 g of PDMS crosslinker produced by the procedure described in Example 1 in 241.6 g of 1-propanol. This solution is charged to the reactor and cooled to 8° C. The solution is degassed by evacuating to less than 15 mBar, holding at vacuum for 15 minutes, and then re-pressurizing with dry nitrogen. This degas procedure is repeated for a total of 3 times. The reactor is held under a blanket of dry nitrogen.

In a separate flask, a monomer solution is prepared by mixing 1.05 g of cysteamine hydrochloride, 25.83 g of DMA and 11.07 g of methoxy poly(ethylene glycol) acrylate (molecular weight=454) and 140 g of 1-propanol in the same manner as described in Example 4. This solution is filtered with a Waterman 540 filter paper, and then added to the reactor through a degas unit and HPLC pump with a flow rate of 3.0 mL/minute. The reaction temperature is then elevated to 68° C. with a heating ramp about one hour.

In a second flask, initiator solution was prepared dissolving 0.1 g of AIBN in 40 mL of 1-propanol. The solution is degassed 3 times by evacuation to 80 mBar, holding vacuum for 5 minutes, and then re-pressurizing with nitrogen.

In a third flask, a feeding solution is prepared by mixing 1.95 g of cysteamine hydrochloride and 198.4 g of 1-propanol and then filtering with Waterman 540 filter paper. This solution is cycled through the degasser/HPLC pump for several minutes.

When the reactor temperature reaches 68° C., the initiator solution is injected into the reaction flask, and the dosing pump is activated, feeding the cysteamine into the reactor through the degasser/HPLC pump over 2 hours. The reaction is then continued at 68° C. for an additional 6 hours, on which heating is discontinued and the reactor is allowed to cool to room temperature.

The reaction mixture is transferred to a flask and stripped solvent at 40° C. under vacuum on a rotary evaporator until 1000 g of sample remain. The solution is then slowly mixed with 1000 g of deionized water with rapid agitation. Additional solvent is further removed until about 1000 g of sample remain. During this stripping process, the solution gradually becomes an emulsion. The resulting material is purified by ultrafiltration over a 10 kD molecular weight cut-off membrane until the permeate conductance is below 2.5 μS/cm.

The purified copolymer solution is acrylated in the same manner as described in Example 3 except that 7.99 g of NaHCO$_3$ and 11.59 mL of acryloyl chloride are used for the reaction. The product is purified by ultrafiltration again with 10 kD molecular weight cut-off membrane until the permeate conductance is as below 2.5 μS/cm. The final macromonomer is isolated by lypophilization.

B. Preparation of Contact Lenses

The macromonomer from step A. above is formulated by the same manner as described in Example 4 except that the solution is concentrated to a final weight with 65.0% of solid.

The above formulation is used to cast lenses following the process as described in Example 4.

Table 2 lists the characteristics of the lenses produced in Examples 6 and 7:

| Example | Elongation to Break, % | E' Modulus MPa | % NVE (in IPA) |
|---|---|---|---|
| Example 6 | 240% | 1.11 | 4.6% |
| Example 7 | 295% | 0.73 | 8.4% |

Example 8

A. Preparation of the Crosslinkable Copolymer

A 2-L jacketed reactor is equipped with a heating/chilling loop, septum inlet adapter, reflux condenser with N$_2$-inlet adapter, and overhead stirring. A solution is generated by dissolving 54.86 g of PDMS-DAm produced by the procedure described in Example 1 and 6.24 g of the PDMS-DAm produced by Example 2 in 200 g of 1-propanol. This solution is charged to the reactor and cooled to 8° C. The solution is degassed by evacuating to less than 5 mBar, holding at vacuum for 15 minutes, and then re-pressurizing with dry nitrogen. This degas procedure is repeated for a total of 5 times.

In a separate 500 mL flask equipped with magnetic stirring and a vacuum-inlet adapter with valve, 2.84 g of cysteamine hydrochloride is dissolved in 140 g of 1-propanol. In another 500 mL flask equipped with magnetic stirring and vacuum-inlet adapter with valve, a solution of 28.84 g of N,N-dimethylacrylamide (Bimax Corporation) and 7.21 g of hydroxyethyl acrylate (Aldrich) were dissolved in 210 g of 1-propanol. In a 125 mL flask, similarly equipped, 0.14 g of azo-bis(isobutyronitrile) (Aldrich) is dissolved in 14 g of 1-propanol. And in a fourth, 100 mL flask, 0.72 g of hydroxyethyl acrylate and 2.88 g of N,N-dimethylacrylamide were dissolved in 21 g of 1-propanol. All four solutions were degassed twice by evacuation to 60 mBar, holding vacuum for 5 minutes, and then re-pressurizing with nitrogen.

Under a positive flow of nitrogen, the reactor is opened and the cysteamine hydrochloride and the larger of the two N,N-dimethylacrylamide/hydroxyethylacrylate solutions were charged to the reactor. Still holding at 8° C., the reactor is degassed by evacuating to less than 5 mBar and holding for 5 minutes, then re-pressurizing with nitrogen. A total of four degassing cycles were performed. The solution containing 0.72 g of hydroxyethyl acrylate and 2.88 g of N,N-dimethylacrylamide is charged to the reservoir of an Alltech 301 HPLC pump equipped with an Alltech 590516 in-line degassing unit. The outlet is positioned to return fluid to the reservoir, and the pump is run at a rate of 0.146 mL/min for 30 minutes to further deoxygenate the solution.

The reactor is then heated to 68° C., and the HPLC pump is stopped and its outlet affixed to drop fluid into the reaction mixture without contacting the walls of the vessel. When at temperature, the azobis(isobutyronitrile) solution is injected into the reactor with a syringe and the HPLC pump is started. The solution is dosed to the reactor over three hours, and then 10 mL of filtered propanol is run through the HPLC lines into the reactor as a rinse. The reactor is then cooled to room temperature.

The reaction mixture is then transferred to a flask and vacuum stripped at 40° C./100 mBar on a rotary evaporator to remove 1-propanol. After the first 344 g of 1-propanol is removed, 500 g of water were added slowly with stirring to create an emulsion. The emulsion is then further stripped of 1-propanol until 473 g of distillate were collected. 600 g of water were again added back to the emulsion, and solvent-exchange is continued to collect a final 150 g of distillate. This emulsion is then acrylated with 6.2 mL of acryloyl chloride by the procedure described in Example 3. The emulsion is then drained from the reactor, diluted to 3.5 L and filtered to 16 μm exclusion. The emulsion is purified by diafiltration (nominal molecular weight cut-off, 10,000D) with deionized water until the permeate conductance is below 2.5 μS/cm, and polymer is isolated by lyophilization.

B. Preparation of Contact Lenses 20.71 g of polymer produced by the above method are dissolved in 107.34 g of 1-Propanol and filtered to 17 μm exclusion. 117.83 g of product are recovered at 16.22% solids. 4.78 g of a 1% Irgacure-2959 solution in 1-Propanol were added, and the solution is concentrated on a rotary evaporator a total weight of 29.40 g.

The above formulation is dosed into polypropylene molds and irradiated for 13.22 seconds under a UV light having intensity of 1.89 mW/cm$^2$. The lenses are deblocked with an 80/20 (v/v) mixture of isopropanol and water, and then hydrated by soaking in water for a day. The lenses have the following properties:

Table 3 lists the characteristics of the lenses produced in Example 8:

| Example | Water content % | E' Modulus MPa | % NVE (in methanol) |
|---|---|---|---|
| Example 8 | 24.5% | 0.7 | 4.5% |

E' Modulus is measured on a Vitrodyne tensile testing instrument. Water content is measured by weighing the wet lenses, then drying at 50° C. under vacuum (<10 mBar), and weighing the dry lenses. The difference expressed as a percent of wet lens weight is the water content.

Extractables are measured according to the procedure described in Example 3. Methanol is used in extraction for this Example 8.

Example 9

A 2-L jacketed reactor is equipped with a heating/chilling loop, septum inlet adapter, reflux condenser with N$_2$-inlet adapter, and overhead stirring. A solution is generated by dissolving 48.76 g of PDMS-DAm produced by the procedure described in Example 1 and 17.71 g of PDMS-DAm produced by the procedure described in Example 2 in 150 g of 1-propanol. This solution is charged to the reactor and cooled to 8° C. The solution is degassed by evacuating to less than 5 mBar, holding at vacuum for 15 minutes, and then re-pressurizing with dry nitrogen. This degas procedure is repeated for a total of 5 times.

In a separate 500 mL flask equipped with magnetic stirring and a vacuum-inlet adapter with valve, 1.93 g of cysteamine hydrochloride is dissolved in 300 mL of 1-propanol. In another 500 mL flask equipped with magnetic stirring and vacuum-inlet adapter with valve, a solution of 31.27 g of N,N-dimethylacrylamide (Bimax Corporation) is dissolved in 300 mL of 1-propanol. In a third flask, similarly equipped, 0.35 g of azo-bis(isobutyronitrile) is dissolved in 150 g of 1-propanol. All three solutions are degassed twice by evacuation to 60 mBar, holding vacuum for 5 minutes, and then re-pressurizing with nitrogen.

Under a positive flow of nitrogen, the reactor is opened and the cysteamine hydrochloride, N,N-dimethylacrylamide, and azo-bis(isobutyronitrile) solutions are charged to the reactor. Still holding at 8° C., the reactor is degassed by evacuating to less than 5 mBar and holding for 5 minutes, then re-pressurizing with nitrogen. A total of four degassing cycles are performed. A sample of the reaction mixture is taken. The reactor is then heated to 68° C. and held at temperature under nitrogen with stirring. The reactor is sampled as soon as the temperature reached 68° C., and again at 0.5 hours after reaching 680, at 1.63 hours, at 2.5 hours, at 4.5 hours, and at 19 hours. These samples are stored at −10° C. until ready for analysis.

The samples are analyzed by gas chromatography to determine the consumption of N,N-dimethylacrylamide. The chromatography is performed on an Agilent 6890 apparatus, using split-less injection in a 250° C. inlet, using a DB-1 column, helium mobile phase, isobaric at 7.7 psi. A flame ionization detector is used. The oven of the GC is programmed to start and hold at 100° C. for 10 minutes; to ramp at 5° C./min to 175° C.; to ramp then at 15° C./min to 325° C.; and then to hold at 325° C. for five minutes. N,N-dimethylacrylamide amounts are quantified by area counts against known standards, by methods known to those skilled in the art.

Example 10

A 2-L jacketed reactor is equipped with a heating/chilling loop, septum inlet adapter, reflux condenser with $N_2$-inlet adapter, and overhead stirring. A solution is generated by dissolving 50.83 g of PDMS-DAm produced by the procedure described in Example 1 and 12.93 g of PDMS-DAm produced by the procedure described in Example 2 in 150 g of 1-propanol. This solution is charged to the reactor and cooled to 8° C. The solution is degassed by evacuating to less than 5 mBar, holding at vacuum for 15 minutes, and then re-pressurizing with dry nitrogen. This degas procedure is repeated for a total of 5 times.

In a separate 500 mL flask equipped with magnetic stirring and a vacuum-inlet adapter with valve, 2.86 g of cysteamine hydrochloride is dissolved in 300 mL of 1-propanol. In another 500 mL flask equipped with magnetic stirring and vacuum-inlet adapter with valve, a solution of 20.53 g of hydroxyethylacrylate and 17.57 g of N,N-dimethylacrylamide is dissolved in 300 mL of 1-propanol. In a third flask, similarly equipped, 0.12 g of azo-bis(isobutyronitrile) is dissolved in 150 g of 1-propanol. All three solutions are degassed twice by evacuation to 60 mBar, holding vacuum for 5 minutes, and then re-pressurizing with nitrogen.

Under a positive flow of nitrogen, the reactor is opened and the cysteamine hydrochloride and monomer solutions are charged to the reactor. Still holding at 8° C., the reactor is degassed by evacuating to less than 5 mBar and holding for 5 minutes, then re-pressurizing with nitrogen. A total of four degassing cycles are performed. The reactor is then heated to 68° C. and held at temperature under nitrogen with stirring. The degassed azo-bis(isobutyronitrile) solution is injected into the reaction mixture and a sample is withdrawn. The reactor is sampled again at 1 hour after reaching 680, at 2 hours, at 5 hours, at 18.75 hours, and at 21 hours. These samples are stored at −10° C. until ready for analysis. The samples are analyzed by gas chromatography to determine the consumption of N,N-dimethylacrylamide as per the method described in Comparative Example 8. The data are shown in the following table:

Table 4 lists the consumption of DMA, % with time for Example 9 and 10:

| Time (Hr) | Example 9 Consumption of DMA, (%) | Example 10 Consumption of DMA, (%) |
| --- | --- | --- |
| 0 | 10 | 0 |
| 0.5 | 20 | — |
| 1 | 90 | 30 |
| 2 | 95 | 55 |
| 3 | 95 | — |
| 5 | — | 70 |
| 18 | — | 90 |

In the Example 10, the monomer mixture is equimolar HEA:DMA. The above data indicate the reactivity of the DMA in the Example 10 is much lower than when DMA is the sole monomer in the Example 9.

What is claimed is:

1. An actinically or thermally crosslinkable prepolymer that is obtained by:
   (a) making a copolymerization product by copolymerizing a polymerizable mixture to obtain a copolymer with first functional groups, wherein the polymerizable mixture comprises a first hydrophilic monomer, at least one polysiloxane-containing crosslinker, a chain transfer agent having a first functional group, a second hydrophilic monomer; and
   (b) reacting an organic compound having a second functional group with the copolymerization product to form the crosslinkable prepolymer having ethylenically unsaturated groups, wherein the organic compound comprises an ethylenically unsaturated group, wherein the second functional group of the organic compound reacts with one of the first functional groups of the copolymerization product, wherein the second hydrophilic monomer is present in an amount sufficient to produce a resultant prepolymer which, after purification, can be crosslinked actinically or thermally to form a silicone hydrogel material, wherein the second hydrophilic monomer has a free radical chain reaction slower than that of the first hydrophilic monomer, wherein the first hydrophilic monomer is (C$_1$-C$_4$-alkyl)acrylamide, N,N-di-(C$_1$-C$_4$-alkyl)acrylamide, or mixture thereof, wherein the second hydrophilic monomer selected from the group consisting of 2-hydroxyethyl acrylate (HEA), glycidyl methacrylate (GMA), N-vinylpyrrolidone (NVP), acrylic acid (AA), and a C$_1$-C$_4$-alkoxy polyethylene glycol (meth)acrylate having a weight average molecular weight of from 200 to 1500, wherein the silicone hydrogel material having about 10% or less of non-volatile extractables, 3. A prepolymer according to claim 1, wherein the first hydrophilic monomer is DMA and the second hydrophilic monomer is a C$_1$-C$_4$-alkoxy polyethylene glycol (meth)acrylate having a weight average molecular weight of from 300 to 1000.

4. A prepolymer according to claim 1, wherein the first hydrophilic monomer is DMA and the second hydrophilic monomer is HEA.

5. A prepolymer according to claim 1, wherein the first hydrophilic monomer is DMA and the second hydrophilic monomer is a mixture of HEA and AA.

6. A prepolymer according to claim 1, wherein the polysiloxane-containing crosslinker is a polysiloxane of formula

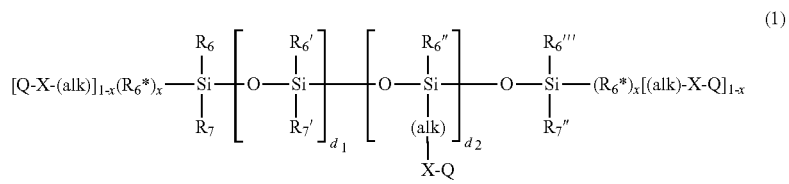
(1)

wherein the polysiloxane-containing crosslinker is a polysiloxane of formula

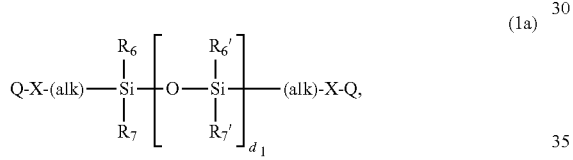
(1a)

wherein R$_6$, R$_6'$, R$_7$ and R$_7'$ are each methyl, d$_1$ is an integer from 10 to 300, (alk) is linear or branched C$_2$-C$_6$ alkylene or a radical —(CH$_2$)$_{1-3}$—O—(CH$_2$)$_{1-3}$—, X is —O— or —NH— and Q is a radical of the formula

(2a)

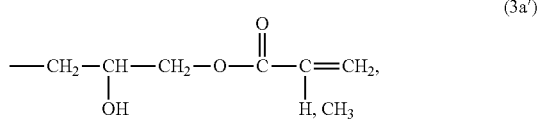
(3a')

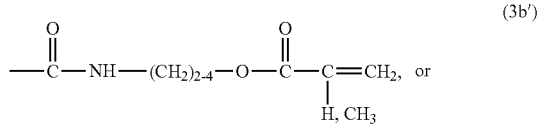
(3b')

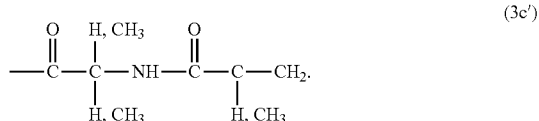
(3c')

2. A prepolymer according to claim 1, wherein the silicone hydrogel material having about 5% or less of non-volatile extractables.

in which (alk) is alkylene having up to 20 carbon atoms which may be interrupted by —O—; X is —O— or —NR$_8$—, R$_8$ is hydrogen or C$_1$-C$_6$-alkyl, Q is an organic radical comprising a crosslinkable or polymerizable group, 80-100% of the radicals R$_6$, R$_6'$, R$_6''$, R$_6'''$, R$_6^*$, R$_7$, R$_7'$ and R$_7''$, independently of one another, are C$_1$-C$_8$-alkyl and 0-20% of the radicals R$_6$, R$_6'$, R$_6''$, R$_6'''$, R$_6^*$, R$_7$, R$_7'$ and R$_7''$, independently of one another, are unsubstituted or C$_1$-C$_4$ alkyl- or C$_1$-C$_4$-alkoxy-substituted phenyl, fluoro(C$_1$-C$_{18}$-alkyl), cyano(C$_1$-C$_{12}$-alkyl), hydroxy-C$_1$-C$_6$-alkyl or amino-C$_1$-C$_6$-alkyl, x is the number 0 or 1, d$_1$ is an integer of from 5 to 700, d$_2$ is an integer from 0 to 8 if x is 0, and is 2 to 10 if x is 1, and the sum of (d$_1$+d$_2$) is from 5 to 700.

7. A prepolymer according to claim 1, wherein the chain transfer agent is an organic primary thiol having a hydroxy, amino, N—C$_1$-C$_6$-alkylamino or carboxy group.

8. A prepolymer according claim 1, wherein the components in step (a) are used in a molar ratio of from 0.5 to 5 equivalents of chain transfer agent:1 equivalent of polysiloxane-containing crosslinker:5 to 60 of equivalents hydrophilic monomer(s).

9. A prepolymer according to claim 1, wherein the copolymer of step (a) is reacted in step (b) with a compound of formula

(4a)

(4b)

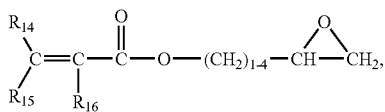

(4c)

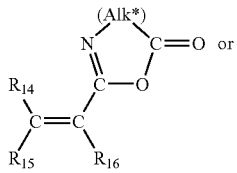

(4d)

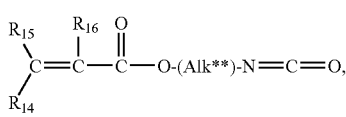

(4e)

wherein $R_{13}$ is halogen, hydroxy, unsubstituted or hydroxy-substituted $C_1$-$C_6$-alkoxy or phenoxy, $R_{14}$, and $R_{15}$ are each independently of the other hydrogen, $C_1$-$C_4$-alkyl, phenyl, carboxy or halogen, $R_{16}$ is hydrogen, $C_1$-$C_4$-alkyl or halogen, $R_{17}$ and $R_{17}'$ are each an ethylenically unsaturated radical having from 2 to 6 C-atoms, or $R_{17}$ and $R_{17}'$ together form a bivalent radical —$C(R_{14})$=$C(R_{16})$— wherein $R_{14}$ and $R_{16}$ are as defined above, and (Alk*) is $C_1$-$C_6$-alkylene, and (Alk**) is $C_2$-$C_{12}$-alkylene.

10. A soft contact lens, comprising a silicon hydrogel material that is obtained by curing a lens-forming material in a mold, wherein the lens-forming material comprises an actinically crosslinkable or polymerizable prepolymer, wherein the prepolymer is obtained by:
(a) copolymerizing a polymerizable mixture to obtain a copolymer with first functional groups, wherein the polymerizable mixture comprises a first hydrophilic monomer, at least one polysiloxane-containing crosslinker, a chain transfer agent having a first functional group, a second hydrophilic monomer; and
(b) reacting an organic compound with the copolymerization product to form the crosslinkable prepolymer having ethylenically unsaturated groups, wherein the organic compound comprises an ethylenically unsaturated group and a second functional group, wherein the second functional group of the organic compound reacts with one of the first functional groups of the copolymerization product, wherein the second hydrophilic monomer is present in an amount sufficient to produce the resultant prepolymer which, after purification, can be crosslinked actinically or thermally to form a silicone hydrogel material, wherein the second hydrophilic monomer has a free radical chain reaction slower than that of the first hydrophilic monomer, wherein the first hydrophilic monomer is ($C_1$-$C_4$-alkyl)acrylamide, N,N-di-($C_1$-$C_4$-alkyl)acrylamide, or mixture thereof, wherein the second hydrophilic monomer selected from the group consisting of 2-hydroxyethyl acrylate (HEA), glycidyl methacrylate (GMA), N-vinylpyrrolidone (NVP), acrylic acid (AA), and a $C_1$-$C_4$-alkoxy polyethylene glycol (meth)acrylate having a weight average molecular weight of from 200 to 1500, wherein the silicone hydrogel material having about 10% or less of non-volatile extractables, wherein the polysiloxane-containing crosslinker is a polysiloxane of formula

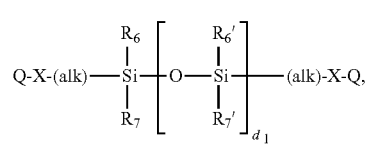

(1a)

wherein $R_6$, $R_6'$, $R_7$ and $R_7'$ are each methyl, $d_1$ is an integer from 10 to 300, (alk) is linear or branched $C_2$-$C_6$ alkylene or a radical —$(CH_2)_{1-3}$—O—$(CH_2)_{1-3}$—, X is —O— or —NH— and Q is a radical of the formula

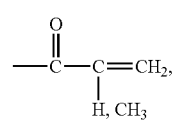

(2a)

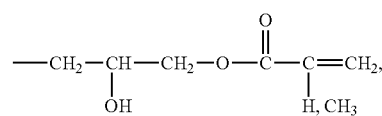

(3a')

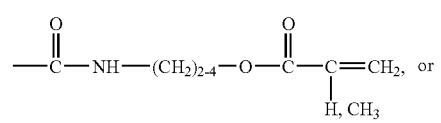

(3b')

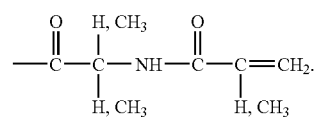

(3c')

11. A soft contact lens of claim 10, wherein the silicone hydrogel material having about 5% or less of non-volatile extractables.

12. A soft contact lens of claim 10, wherein the first hydrophilic monomer is DMA and the second hydrophilic monomer is a $C_1$-$C_4$-alkoxy polyethylene glycol (meth)acrylate having a weight average molecular weight of from 300 to 1000.

13. A soft contact lens of claim 10, wherein the first hydrophilic monomer is DMA and the second hydrophilic monomer is HEA.

14. A soft contact lens of claim 10, wherein the first hydrophilic monomer is DMA and the second hydrophilic monomer is a mixture of HEA and AA.

15. A soft contact lens of claim 10, wherein the polysiloxane-containing crosslinker is a polysiloxane of formula

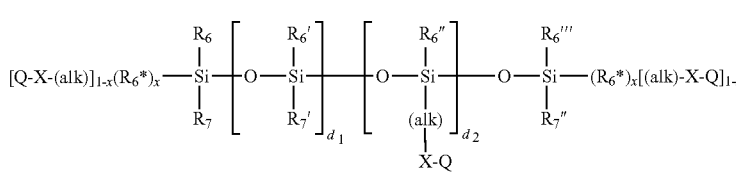

in which (alk) is alkylene having up to 20 carbon atoms which may be interrupted by —O—; X is —O— or —$NR_8$—, $R_8$ is hydrogen or $C_1$-$C_6$-alkyl, Q is an organic radical comprising a crosslinkable or polymerizable group, 80-100% of the radicals $R_6$, $R_6'$, $R_6''$, $R_6'''$, $R_6^*$, $R_7$, $R_7'$ and $R_7''$, independently of one another, are $C_1$-$C_8$-alkyl and 0-20% of the radicals $R_6$, $R_6'$, $R_6''$, $R_6'''$, $R_6^*$, $R_7$, $R_7'$ and $R_7''$, independently of one another, are unsubstituted or $C_1$-$C_4$ alkyl- or $C_1$-$C_4$-alkoxy-substituted phenyl, fluoro($C_1$-$C_{18}$-alkyl), cyano($C_1$-$C_{12}$-alkyl), hydroxy-$C_1$-$C_6$-alkyl or amino-$C_1$-$C_6$-alkyl, x is the number 0 or 1, $d_1$ is an integer of from 5 to 700, $d_2$ is an integer from 0 to 8 if x is 0, and is 2 to 10 if x is 1, and the sum of ($d_1$+$d_2$) is from 5 to 700.

16. A soft contact lens of claim 10, wherein the polysiloxane-containing crosslinker is a polysiloxane of formula

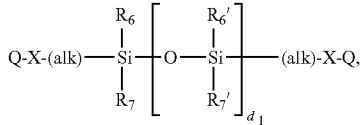

wherein $R_6$, $R_6'$, $R_7$ and $R_7'$ are each methyl, $d_1$ is an integer from 10 to 300, (alk) is linear or branched $C_2$-$C_6$ alkylene or a radical —$(CH_2)_{1-3}$—O—$(CH_2)_{1-3}$—, X is —O— or —NH— and Q is a radical of the formula

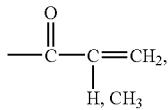

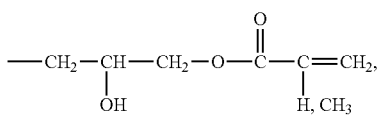

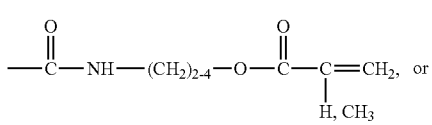

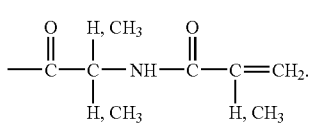

17. A soft contact lens of claim 10, wherein the chain transfer agent is an organic primary thiol having a hydroxy, amino, N—$C_1$-$C_6$-alkylamino or carboxy group.

18. A soft contact lens of claim 10, wherein the components in step (a) are used in a molar ratio of from 0.5 to 5 equivalents of chain transfer agent:1 equivalent of polysiloxane-containing crosslinker:5 to 60 of equivalents hydrophilic monomer(s).

19. A soft contact lens of claim 10, wherein the copolymer of step (a) is reacted in step (b) with a compound of formula

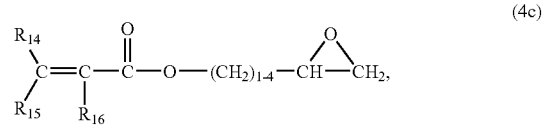

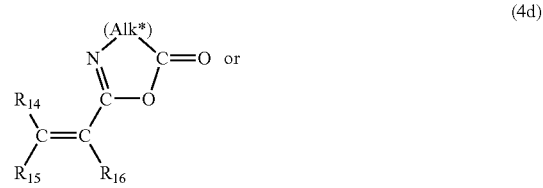

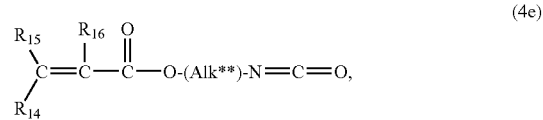

wherein $R_{13}$ is halogen, hydroxy, unsubstituted or hydroxy-substituted $C_1$-$C_6$-alkoxy or phenoxy, $R_{14}$, and $R_{15}$ are each independently of the other hydrogen, $C_1$-$C_4$-alkyl, phenyl, carboxy or halogen, $R_{16}$ is hydrogen, $C_1$-$C_4$-alkyl or halogen, $R_{17}$ and $R_{17}'$ are each an ethylenically unsaturated radical having from 2 to 6 C-atoms, or $R_{17}$ and $R_{17}'$ together form a bivalent radical —C($R_{14}$)=C($R_{16}$)— wherein $R_{14}$ and $R_{16}$ are as defined above, and (Alk*) is $C_1$-$C_6$-alkylene, and (Alk**) is $C_2$-$C_{12}$-alkylene.

* * * * *